United States Patent
Mühlhoff et al.

(10) Patent No.: US 8,808,279 B2
(45) Date of Patent: Aug. 19, 2014

(54) DEVICE AND METHOD FOR MEASURING AN OPTICAL BREAK-THROUGH IN A TISSUE

(75) Inventors: Dirk Mühlhoff, Jena (DE); Michael Kempe, Jena (DE); Markus Strehle, Jena (DE); Mario Gerlach, Glienicke-Nordbahn (DE); Markus Sticker, Jena (DE); Mark Bischoff, Jena (DE); Dick Manfred, Gefell (DE); Michael Bergt, Weimar (DE)

(73) Assignee: Carl Zeiss Meditec AG, Jena (DE)

(*) Notice: Subject to any disclaimer, the term of this patent is extended or adjusted under 35 U.S.C. 154(b) by 1690 days.

(21) Appl. No.: 10/525,424

(22) PCT Filed: Aug. 22, 2003

(86) PCT No.: PCT/EP03/09345
§ 371 (c)(1), (2), (4) Date: Sep. 7, 2005

(87) PCT Pub. No.: WO2004/026198
PCT Pub. Date: Apr. 1, 2004

(65) Prior Publication Data
US 2006/0106371 A1 May 18, 2006

(30) Foreign Application Priority Data

Aug. 23, 2002 (DE) .................... 102 39 213
May 23, 2003 (DE) .................... 103 23 422

(51) Int. Cl.
*A61B 18/18* (2006.01)
(52) U.S. Cl.
USPC .................... 606/4; 606/5; 607/89
(58) Field of Classification Search
None
See application file for complete search history.

(56) References Cited

U.S. PATENT DOCUMENTS

| 5,423,801 A | 6/1995 | Marshall et al. |
| 5,549,599 A | 8/1996 | Sumiya |

(Continued)

FOREIGN PATENT DOCUMENTS

| DE | 196 35 998 C1 | 4/1998 |
| EP | 1 232 734 A1 | 8/2002 |

(Continued)

OTHER PUBLICATIONS

Tibor Juhasz et al., "Time-Resolved Observations of Shock Waves and Cavitation Bubbles Generated by Femtosecond Laser Pulses in Corneal Tissue and Water," *Lasers in Surgery and Medicine*, vol. 19, pp. 23-31 (1996).

Izatt et al., "Micrometer-Scale Resolution Imaging of the Anterior Eye in Vivo With Optical Coherence Tomography," *Arch Ophthalmol*, vol. 112, pp. 1584-1589 (Dec. 1994).

(Continued)

*Primary Examiner* — Gary Jackson
*Assistant Examiner* — Lynsey Crandall
(74) *Attorney, Agent, or Firm* — Patterson Thuente Pedersen P.A.

(57) ABSTRACT

The invention relates to a device for measuring an optical penetration that is triggered in a tissue underneath the tissue surface by means of therapeutic laser radiation which a laser-surgical device concentrates in a treatment focus located in said tissue. The inventive device is provided with a detection beam path comprising a lens system which couples radiation emanating from the tissue underneath the tissue surface into the detection beam path. A detector device generating a detection signal which indicates the spatial dimension and/or position of the optical penetration in the issue is arranged downstream of the detection beam path.

8 Claims, 14 Drawing Sheets

(56) References Cited

U.S. PATENT DOCUMENTS

| | | | |
|---|---|---|---|
| 5,785,651 A | 7/1998 | Kuhn et al. | |
| 5,984,916 A | 11/1999 | Lai | |
| 6,110,166 A | 8/2000 | Juhasz | |
| 6,454,761 B1 * | 9/2002 | Freedman | 606/5 |
| 6,613,041 B1 * | 9/2003 | Schrunder | 606/5 |

FOREIGN PATENT DOCUMENTS

| | | |
|---|---|---|
| GB | 2 317 227 A | 3/1998 |
| WO | WO 01/15592 A2 | 3/2001 |
| WO | WO 01/80792 A2 | 11/2001 |
| WO | WO 01/91661 A1 | 12/2001 |
| WO | WO 02/076319 A1 | 10/2002 |

OTHER PUBLICATIONS

Padawer, "The Nomarski interference-contrast microscope. An Experimental basis for image interpretation," *Journal of the Royal Microscopic Society*, vol. 88, Pt. 3, pp. 305-349 (Jun. 1968).

Karsten König et al., "Nanodissection of Human Chromosomes and Ultraprecise Eye Surgery With Nanojoule Near Infrared Femtosecond Laser Pulses", *Proceedings of SPIE*, vol. 4633 (2002) © 2002 SPIE, pp. 11-22.

Wolfgang Drexler et al., "Ultrahigh-resolution Opthalmic Optical Coherence Tomography", *NIH Public Access Author Manuscript*, Available in PMC Aug. 23, 2007 Published in final edited from as: *Nat Med.* Apr. 2001; 7(4): 502-507, 13 Pgs.

* cited by examiner

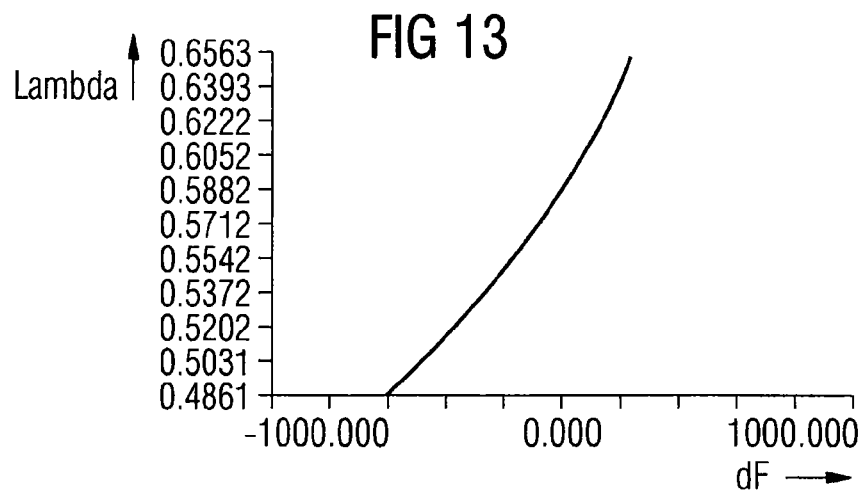
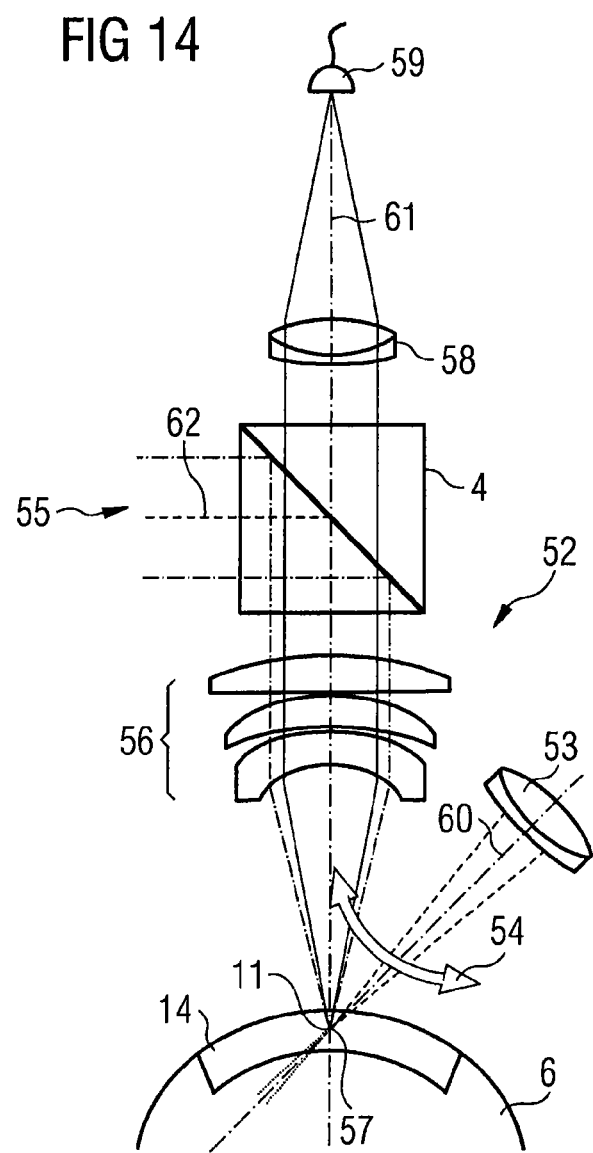

DEVICE AND METHOD FOR MEASURING AN OPTICAL BREAK-THROUGH IN A TISSUE

FIELD OF THE INVENTION

The invention relates to a device for measuring an optical break-through created in a tissue, beneath a tissue surface, by treating laser radiation which a laser surgical unit focuses in a treatment focus located in said tissue, said device having a detection beam path comprising optics. The invention further relates to a method of measuring an optical break-through created in a tissue, beneath a tissue surface, by treating laser radiation.

BACKGROUND OF THE INVENTION

Treating laser radiation is used in laser surgical methods, in particular, for operations in optical surgery. In this connection, the treating laser radiation is focused within the tissue, i.e. beneath the tissue surface, such that an optical break-through is created in the tissue. The treating laser radiation acts through photo disruption or photo ablation.

In the tissue, several processes initiated by the treating laser radiation occur one after the other. If the power density of the radiation exceeds a threshold value, an optical break-through will result, which generates a plasma bubble in the tissue. Said plasma bubble grows after creation of the optical break-through due to expanding gases. If the optical break-through is not maintained, the gas generated in the plasma bubble is absorbed by the surrounding tissue, and the bubble disappears again. However, this process takes very much longer than the forming of the bubble itself. If a plasma is generated at a tissue boundary, which boundary may quite well be located within a tissue structure as well, tissue will be removed from said boundary. Therefore, this is then referred to as photo ablation. In connection with a plasma bubble which separates tissue layers that were previously connected, one usually speaks of photo disruption. For the sake of simplicity, all such processes are summarized here by the term optical break-through, i.e. said term includes not only the actual optical break-through, but also the effects resulting therefrom in the tissue.

For a high accuracy of a laser surgical method, it is indispensable to guarantee high localization of the effect of the treating laser beams and to avoid, if possible, collateral damage to adjacent tissue. It is, therefore, common in the prior art to apply the treating laser radiation in a pulsed manner, so that the threshold value for the power density of the treating laser radiation required to cause an optical break-through is exceeded only during the individual pulses. In this regard, U.S. Pat. No. 5,984,916 clearly shows that the spatial area of the optical break-through (in this case, of the generated interaction) strongly depends on the pulse width. Therefore, high focusing of the laser beam in combination with very short pulses allows placing of the optical break-through in a tissue with in a very punctiform manner.

The use of pulsed treating laser radiation was recently established in ophthalmology, particularly for correction of visual deficiencies. Visual deficiencies of the eye often result from the fact that the refractive properties of the cornea and of the lens do not cause proper focusing on the retina. In the case of nearsightedness (also referred to as myopia), the focus is located in front of the retina when the eye is relaxed, whereas in the case of farsightedness (also referred to as hyperopia), the focus is located behind the retina.

U.S. Pat. No. 5,984,916 mentioned above, as well as U.S. Pat. No. 6,110,166, describe methods of correcting visual deficiencies by means of suitably generating optical break-throughs, so that, ultimately, the refractive properties of the cornea are selectively influenced. A multitude of optical break-throughs are joined such that a lens-shaped partial volume is isolated within the cornea of the eye. The lens-shaped partial volume which is separated from the remaining corneal tissue is then removed from the cornea by means of a laterally opening cut. The shape of the partial volume is selected such that, with the volume removed, the refractive properties of the cornea are changed so as to generate the desired correction of visual deficiency.

In order to isolate the partial volume, it is indispensable, of course, to generate the optical break-throughs at predetermined sites. U.S. Pat. No. 5,984,916 describes corresponding sensors which sense the cross-section as well as the position and intensity of the treating laser beam and feed a corresponding control unit, which influences the laser treatment beam such that an optical break-through is achieved at the desired target point.

In contrast thereto, EP 1,232,734 A1 suggests to use a wavefront sensor to determine the position of an optical break-through which has been generated in an eye. In this connection, said publication states that the bubble size can be measured by the wavefront sensor using "relatively well-known wavefront techniques". Unfortunately, this document remains silent as to how such measurement could be effected. It does not convey any technical teaching, but merely states a problem to be solved. However, since a wavefront sensor is known to be capable of determining a distortion of a wavefront, it would be conceivable to achieve the object mentioned in EP 1,232,734 A1 as the problem to be solved by using a wavefront sensor to detect a deformation of the corneal front surface created by a bubble generated inside the cornea. However, in such a conceivable approach it would have to be expected that the precision of measurement strongly decreases as the size of the bubble decreases, because a smaller bubble will certainly also lead to a strongly reduced deformation of the front surface of the cornea. Moreover, it would have to be expected that, for a bubble located at a greater depth, the bubble diameter indicated by this type of measurement would be smaller than for a bubble of the same size located higher up. Thus, in such an approach an error of measurement as a function of the depth position of the bubble would have to be expected.

The precision with which treating laser radiation can be applied to a patient's eye to correct a visual deficiency, for example, naturally has a direct effect on the quality of the result, i.e. in the example mentioned, on the quality of an optical correction. Therefore, it is an object of the invention to provide a device for measuring an optical break-through by which an increased selectivity of the effect of treating laser radiation can be achieved.

SUMMARY OF THE INVENTION

This object is achieved by a device for measuring an optical break-through created in a tissue, beneath a tissue surface, by treating laser radiation which a laser surgical unit focuses in a treatment focus, said focus being located in the tissue, wherein said device has a detection beam path comprising optics, in that the optics couple radiation emitted by the tissue, from beneath the tissue surface, into the detection beam path, and in that a detector unit is arranged following the detection beam path, said detector unit generating a detection signal which indicates the spatial extent and/or position of the optical break-through in the tissue. The object is further achieved by a method of measuring an optical break-through created in a tissue, beneath a tissue surface, by treating laser radiation, wherein radiation emitted by the tissue, from beneath the tissue surface, is detected and a measure of the spatial extent and/or position of the optical break-through is determined therefrom.

Thus, in the concept according to the invention, the spatial extent and/or position of the optical break-through is detected and, for this purpose, radiation is analyzed which is emitted by the tissue itself, i.e. from beneath the tissue surface. The term "emitted" summarizes back-scattered, reflected or induced radiation in contrast to transmitted radiation. The method according to the invention as well as the device according to the invention are suitable, in particular, for measurements during treatment of transparent or semi-transparent tissue, respectively, because, in this case, up to three-dimensional structural information can be obtained. Thus, the invention is suitable, in particular, for monitoring microsurgical operations on the eye.

The detection signal can be used to control the treatment radiation in numerous ways. Thus, on the one hand, a detection signal indicating the extent of an optical break-through can be used to control laser parameters, e.g. the beam cross-section, the radiation intensity and/or the pulse width. In this connection, manual setting by a viewer to whom the detection signal is presented is possible as well as a partially automatic or fully automatic dosed-loop control. In this case, influencing the treating laser radiation may influence parameters which form the beam as well as deflection parameters which spatially control the beam in the tissue. Sensing the spatial extent of the optical break-through is primarily a question of influencing the parameters which control the beam properties, whereas a detection signal indicating the position of the optical break-through in the tissue is particularly suitable for control of a deflecting unit and, thus, allows the laser beam to be guided by means of closed-loop control.

The detection signal generated by the detector unit can preferably be used directly for closed-loop control of the treating laser radiation. In doing so, the loop is closed, by using the actual optical break-through which is formed or which acts in the tissue. This is more direct than the use of indirect measures which are obtained prior to the interaction with the tissue. Detection of the radiation coming from the tissue enables much more exact closed-loop control of the treating laser radiation, because the optical break-through is directly detected. The sensing of treating laser radiation parameters before entering the tissue, as hitherto suggested in the prior art, is much more indirect, because the interaction with the tissue is left unconsidered, whereas the approach according to the invention provides direct closed-loop control.

Particularly preferred for the treating laser radiation are ultra-short laser pulses having pulse widths of between 1 fs and 100 ps in the infra-red or visible spectral range (400 to 1900 nm). This optical radiation can penetrate tissue, in particular the transparent parts of the eye (cornea, lens, vitreous body). At high power densities, which are only achieved in the focal point, the laser pulses trigger non-linear optical processes in the form of optical break-throughs, such as created, for example, by multiphoton excitation or frequency conversion. The required power density may be specific to the tissue.

The invention is suitable, in particular, for the aforementioned surgical method provided for correction of visual deficiencies. In addition, the invention may also be used for further ophthalmological operations or other surgical operations. These include cuts for refractive optical surgery or for removal of enclosed foreign bodies, cuts in the cornea, cuts in the vitreous body of the eye, in the lens or in the sclera. Localized, laser-induced changes of the tissue without cutting, which reduce turbidity or hardening of the cornea, are also a field in which to employ the invention. Moreover, other tissues, such as the dermis, for example, are also transparent to infrared radiation. A suitable selection of the wavelength of the treating laser radiation will enable diagnosis and treatment in these tissues, too. The invention is suitable for processing of tissue in vitro as well. Thus, histological examinations can be carried out, for example, in an extracted piece of tissue. The treating laser beam may be used to carry out a histological section in a tissue region which may have been measured before. The cutting properties of the ultra-short laser pulses have an advantageous effect on the quality of the section; collateral damage to tissue is largely excluded.

Optical break-throughs always have an effect on tissue. In most cases, an optical scattering center, e.g. in the form of a plasma bubble, is formed for at least a short time. It is therefore preferred to determine the spatial extent and/or position of scattering centers generated by the optical break-through.

In a particularly advantageous embodiment of the invention, the radiation emitted by the tissue may be back-scattered radiation coming from an illumination radiation source. Therefore, a further embodiment comprising an illumination radiation source, which couples illumination radiation into the tissue, is preferred. In the method according to the invention, observation radiation is advantageously irradiated into the tissue, and radiation emitted by the tissue in the form of back-reflection is evaluated. Illumination radiation and treatment radiation may be derived from the same source of radiation, e.g. by using an energy reducer which can be switched on.

As an alternative to illumination which is externally coupled in, radiation generated by the break-through itself or back-scattered components of the treating laser radiation may be used for detection.

Detection of the position of the optical break-through in a manner suitable to guide the laser beam in the aforementioned surgical method requires precision which is given by a desired correction of defective vision. Depending on the optical application, a difference in thickness of about 12 µm between the center and the edge of a volume to be isolated can cause a change in the refractive power of the cornea of one diopter. A correspondingly exact spatial measurement of the position of the optical break-through is, therefore, very advantageous, in particular, for applications in ophthalmological surgery.

In a first embodiment of the invention, an interferometric detection of the radiation emitted by the tissue is effected, and the device comprises an illumination radiation source which, together with the detection beam path, is part of an interferometer structure. Conveniently, back-scattered radiation is detected and the information concerning the optical break-through generated by the treating laser radiation, in particular the localization of the optical break-through with respect to adjacent layers of tissue, is obtained from radiation scattered back from the location of the focus of the illumination radiation. The amount of back-scattered radiation bears information on discontinuities in refractive index, which appear both at the boundary of different types of tissue (e.g. between the stroma and the Bowman's membrane of the cornea) as well as at the location of the optical break-through both below and above the threshold to photo disruption and photo ablation.

In a particularly convenient embodiment, such interferometer structure may be provided, for example, as an optical coherence tomograph, which spatially filters, in a suitable form, radiation emitted by the tissue, e.g. back-reflected or scattered illumination radiation. In this case, spatial filtering is effected such that the optical break-through is localized with sufficient precision. If the illumination radiation is incident along an optical axis, the spatial filtering can be achieved laterally, i.e. perpendicular to the optical axis, by means of suitable focusing of the illumination radiation. The focus position of the illumination radiation then laterally defines the measurement volume in which an optical break-through is detected or measured, respectively. In an optical coherence tomograph, the localization of the measurement volume can be achieved in an axial direction by using short temporal coherence for the illumination radiation. Interference then occurs only in the back-reflection from the measured volume, and the presence of interference shows that radiation was scattered back from a known depth within the tissue. Since the optical break-through, as already mentioned, is associated with the formation of a photo disruption bubble or a plasma bubble and separates layers of tissue, the optical break-through is characterized by back-scattering of illumination radiation which is locally increased in a significant manner. Thus, the position of the back-scattering of the radiation emitted from the area of the optical break-through on the optical axis of detection is preferably determined by the occurrence of interference.

In this respect, the interferometer structure preferably comprises a measuring arm and an adjustable reference arm. The coherence length of the illumination radiation determines the axial resolution, because interference occurs only, if the lengths of the measuring arm and of the reference arm differ by less than the coherence length of the illumination radiation. In combination with the lateral discrimination by the focusing of the illumination radiation, the effect is, in summa, a three-dimensional spatial detection of the optical break-through, with the diameter of the focusing defining the lateral resolution and the coherence length of the illumination radiation defining the depth resolution.

In order to scan a larger area for optical break-throughs, it is convenient that the source of illumination radiation focus the illumination radiation in an illumination focus located in the tissue, with the position of said focus being adjustable to generate the detection signal. In this case, the adjustment is advantageously effected with respect to the position of the focus of the treating laser radiation. In order to obtain a device which is structured as simply as possible and is as compact as possible, preferably the same optics direct treating the laser radiation and the illumination radiation onto the tissue to be treated, e.g. the cornea of an eye. In most cases, this is achieved by combining the illumination radiation and the treating laser radiation via an optical combiner, e.g. by using a beam splitter. The focusing optics, through which both beams then pass together, generate a focus which is located approximately at the same location laterally and, depending on the beam divergence before said combination, also axially.

An independent lateral displacement of the illumination radiation relative to the treating laser radiation can be achieved by providing an adjustable deflecting unit, e.g. a scanner, upstream of said combiner. The focus position of the illumination radiation can be axially adjusted by adapting the divergence of the illumination radiation before combining it with the treating laser radiation. In an analogous manner, the size of the focus can be changed relative to the treating laser radiation by suitably pre-conditioning the diameter of the illumination radiation beam.

Therefore, it is preferred, in this respect, that the illumination radiation be coupled into a light path of the illumination laser radiation, wherein use is made of adjustable optics, by which the divergence of the illumination radiation is changeable independently of the divergence of the treating laser radiation.

In an optical coherence tomograph, the observation of the optical break-through is preferably effected by axial adjustment of the spatial selection of the back-scattered radiation, including the location of the optical break-through. This allows to observe the axial extent of the optical break-through and its position and to obtain the detection signal. The heterodyne detection of the back-scattered radiation effected by the optical coherence tomograph preferably uses an illumination radiation having as large a bandwidth as possible, preferably around an average wavelength of 850 nm. The bandwidth is inversely proportional to the coherence length of the observation radiation which also determines the axial resolution of the optical coherence tomograph in said heterodyne detection. Using different wavelengths for the illumination radiation and the treating laser radiation, a superposition and separation of both optical paths can be easily effected by dichroic beam splitters.

There are, in principle, two possibilities to realize the aforementioned axial displacement of the focus:
a) If the focus diameter of the illumination beam path is greater than that of the treating laser beam, sensing can be achieved by suitably detuning the interferometer, e.g. by adjusting the measuring arm. The axial resolution is then mainly determined by the coherence length of the illumination radiation and is typically in the order of magnitude of 10 μm. The detuning range axially defines the measuring range.
b) If the focus diameter of the illumination radiation and of the treating laser radiation are similar in size, axial sensing requires synchronous detuning of the interferometer and of the focus position. The latter can be effected by means of the adjustable optics, by which the divergence of the illumination radiation can be changed without changing the divergence of the treating laser radiation, before combining the illumination radiation and the treating laser radiation. The axial resolution of the detection of the optical break-through then depends on both the depth of focus of the optical projection, which is inherently confocal due to the heterodyne detection, and on the coherence length of the illumination radiation and is below the aforementioned resolution for case a).

The higher resolution achieved in case b) is, of course, beneficial also to lateral sensing of the area in which the optical break-through is expected or generated, respectively. On the other hand, an increased speed of adjustment is required in order to sense an area of a certain size within the same length of time.

A further possibility of spatial selection of the radiation emitted by the tissue, from which radiation the detection signal is obtained, is the use of confocal imaging. In a second embodiment of the invention, it is therefore preferred that the detector unit senses the radiation emitted by the tissue by means of confocal imaging, wherein the spatial extent of the optical break-through is preferably determined by adjusting the focus of confocal imaging. The device then has a structure similar to that of a laser-scanning microscope, which operates by reflection according to the incident-light method.

The confocal principle allows a specific volume element in the tissue to be projected onto the detector and to suppress any radiation from the tissue which is emitted by volume elements other than said specific volume element. In particular, there is a strong suppression of radiation from layers deeper down or higher up. The confocality condition between the sensed volume element and the projection onto the detector, which projection is usually effected through a pinhole lens, ensures that, with a suitable chromatic correction, radiation of any wavelength arrives at the detector as long as such radiation only comes from the selected volume element.

The confocally detected radiation may either come from the optical break-through itself, being back-scattered treating laser radiation, for example, or may be back-scattered illumination radiation. Particularly advantageously, the latter can be introduced into the beam path of the treating laser beam by means of a dichroic beam splitter. In this connection, an axial displacement of the selected volume element is obtained by a focus adjustment in the confocal imaging, as it is known from laser scanning microscopes. It is therefore preferred that the detector unit generates the detection signal by adjusting the focus of confocal imaging, preferably along the ray direction of the treating laser radiation. For this purpose, the adjustable optics already mentioned for the first embodiment can be used, said optics changing the divergence of the illumination radiation without changing the divergence of the treating laser radiation. Using this construction, a compact structure is achieved, because the treating laser radiation and the illumination radiation are focused in the tissue via the same optics.

Since in confocal detection the axial resolution is inseparably linked with the size of the focus spot, to achieve a high resolution requires focusing the illumination radiation in the tissue as narrowly as possible. An axial resolution of approx. 10 μm requires a focus diameter of approx. 3 μm. This may be achieved, relatively independently of the focusing of the treating laser radiation, by suitably illuminating the objective which focuses the radiation in the tissue.

During confocal detection, sensing with a lateral resolution may be effected in a known manner by suitably deflecting the illumination beam or the focus, respectively, in a lateral direction, i.e. transversely to the optical axis.

In a third embodiment of the invention, the axial adjustment of the volume element selected in confocal detection can be largely dispensed with. For this purpose, the basic principle of confocal detection is modified such that a dispersive element, e.g. optics provided with a certain dispersion, is now used for confocal imaging. If the selected volume element emits white light, i.e. radiation which is composed of different spectral components, such as red, green or blue light, only from a certain depth of the sample are certain spectral components focused exactly into the pinhole and thus projected onto the detector through the optics. For a certain volume element, components having a shorter wavelength (blue light, for example) have a focus on the optical axis between the pinhole and the pinhole optics, and diverge again until they arrive at the detector, so that only a small part of the radiation of this spectral component can pass through the pinhole and reach the detector. Consequently, these components are very effectively suppressed. The same applies to components having a longer wavelength (e.g. red light), because the focus assigned to them is located behind the pinhole, but the beams are blocked before by the pinhole. Only a specific central spectral component (green light, for example) is projected by the optics from the white-light emitting volume element through the pinhole.

In contrast thereto, a further white-light emitting volume element, which is arranged on the optical axis between the volume element just considered and the optics, may guide shorter-wavelength radiation components into a focus located in the pinhole. The same applies to a volume element which, as seen from the optics, is located behind the volume element first considered. From there, only the long-wavelength components are focused exactly on the pinhole and can be detected.

According to the third embodiment, in white-light emitting or back-scattering optical break-throughs, the spectral composition of the detected radiation consequently encodes information concerning the depth from which the radiation comprising the respective spectral component comes. The dispersive element causes a focus shift for certain spectral components of the detected radiation, said shift corresponding to the desired axial resolution. In this embodiment, the detector for receiving the radiation is therefore preferably provided behind the pinhole with spectral selective or resolving properties, e.g. a multi-channel spectrometer. In the simplest case, the spectrometer may comprise only two or three channels.

The channels of the spectrometer are then read and evaluated, and the position, on the optical axis, of the volume element scattering or emitting the radiation can be determined from the level of the individual signals relative to each other. Moreover, advantageously, the size of a radiating volume element may also be determined. If a very small radiating volume element is present, a distinct signal will be output by only one channel of the multi-channel spectrometer, in a transition region, i.e. at an average volume size, two channels will show such distinct signal, but never all three spectral channels. If, however, a very large radiating volume element is present, the spectrometer will display approximately the same signal intensity in several channels, for example in all three channels. The width of the spectral distribution detected by the spectrometer thus provides a measure of the size of the volume element, with the size along the optical axis being decisive.

A possible design of the third embodiment relates to the kind of radiation analyzed in the detection beam path. Various alternatives exist. On the one hand, direct emission of a plasma bubble generated by an optical break-through may be used, because the plasma emits within a broad spectrum during the process of disruption. Alternatively, the already mentioned external illumination may be resorted to, for which purpose, for example, a white-light LED, a thermionic emitter, a suitably broadband laser or a superluminescence diode may be used.

In an embodiment that is particularly easy to realize, several independently controllable sources of radiation differing from one another regarding their spectral properties can be used, e.g. red, green and blue LEDs. These individual, spectrally different sources of radiation are sequentially operated, so that the detector no longer has to have spectral resolution. The information for the individual color channels is obtained in a time sequence, so that evaluation is effected as already mentioned above. It is, therefore, preferred that the source of illumination radiation comprise a plurality of radiation source elements, which are individually operable and have different spectral properties, so that spectrally selective sensing is obtained by sequentially operating said radiation source elements. Spectrally different illumination radiation is sequentially irradiated and the recording of the radiation emitted by the tissue, in turn, occurs sequentially, to achieve the corresponding spectral association.

The aforementioned embodiments, wherein the detection beam path and the illumination beam path are incident essentially on a common optical axis, achieve a unit having a very compact structure. Desirable information on structures located on the optical axis behind the optical break-through, may be obtained only with great difficulty, in some cases, because the optical break-through often has a shading effect on radiation from layers of tissue located behind the break-through. For applications, in which detection is desired also in those areas of tissue which are located, as seen from the apparatus, behind the optical break-through, it is therefore convenient for the detection beam path to have an optical axis which is inclined relative to an optical axis of the treating laser radiation or the illumination radiation. Thus, the emitted radiation is detected along an optical axis, which is oblique relative to an optical axis along which the treating laser radiation or observation radiation is radiated into the tissue. This approach allows, for example, to determine the thickness of a cornea while, at the same time, sensing the optical break-through. Determining the thickness in turn allows easy gauging of the dimension of the optical break-through, e.g. of a plasma bubble diameter, because the thickness of the cornea provides a well-known measure, which is usually precisely measured, in particular before ophthalmological operations. Thus, an automatic calibration for measuring the optical break-through is also achieved.

The irradiation oblique to the optical axis of the treating laser radiation is suitable for all of the above-mentioned embodiments of the invention. However, it is useful also, in particular, for a further, fourth embodiment, which further develops the principle known from slit lamps. By means of slit optics, slit illumination can be radiated, for example, into the cornea, oblique to the optical axis of an observation beam path. The points of intersection of the observation beam path and of the slit illumination represent a scattered-light channel from which radiation coming from the slit illumination and scattered in the examined tissue can pass into the observation beam path. If the optical axes of the slit illumination and of the observation beam path are rotated or displaced relative to one another, the point of intersection forming the scattered-light channel will move within the examined tissue. For example, a displacement from the back surface of the cornea to the front surface of the cornea may be effected. An intensity profile recorded in this process will then show not only optical break-throughs forming scattering centers, but also the back and front surfaces of the cornea. The known distance of these two surfaces then gauges the size of the detected scattered-light center, thus of the optical break-through; accordingly, a kind of "auto-calibration" is provided.

Therefore, in a fourth embodiment of the invention, the position of the optical axis of the detection beam path is preferably adjustable relative to the position of the optical axis of the treating laser radiation or of the illumination radiation. Adjustment of the position between the optical axis of detection and irradiation allows information to be obtained on the spatial extent of the optical break-through or of the interaction induced thereby, respectively.

The oblique position of the illumination beam path or of the treating laser beam path and of the detection beam path relative to one another can be employed in the most diverse modifications, in order to determine the position and/or extent of the optical break-throughs. This makes it possible for the optical axes of the observation beam path and of the illumination beam path to be located obliquely relative to one another and to be adjustable relative to one another, independently of the treatment beam path. Alternatively, the treatment beam path can also be combined with the observation beam path via a beam splitter.

The adjustability of the position of the observation beam path and of the illumination beam path can be achieved in any suitable manner by mechanical means. It is particularly easy to effect if an adjustable luminous field is employed, such as that known from DE 198 12 050 A1. The adjustment of the luminous field, which is effected, for example, using a digital mirror array, allows to easily achieve the desired adjustment without complex mechanical assemblies.

An adjustment of the optical axes can be dispensed with, if the observation beam path senses an at least stripe- or line-shaped image of the scattered-light channel. While the variant comprising adjustable optical axes required no projection onto an imaging detector, an image sensor is required if the optical axes of the illumination beam path and of the observation beam path have fixed positions relative to each other. This is particularly advantageous if the illumination beam path is combined and jointly deflected with the treating laser beam in order to generate optical break-throughs at different sites on the tissue. The illumination radiation and the optical break-throughs are always coaxial then. The depth information is obtained by the inclined imaging onto the image sensor.

In a simplified variant of the fourth embodiment, an illumination beam path is dispensed with completely. Instead, the radiation generated directly in the optical break-through is analyzed in the detection beam path. Back-scattering of treating laser radiation also contributes to the generation of the detection signal. Observation is effected in an oblique manner again, using an image sensor in order to obtain the required depth information on the position of the optical break-through.

In a variant of the fourth embodiment, which enables a particularly universal measurement, a scanning deflection is effected transversely of the optical axis of the illumination radiation. This is preferably independent of the illumination beam path that feeds an image sensor. In this case, too, the oblique observation relative to the illumination ensures that the required depth information is obtained.

Such scanning device is generally useful for the device according to the invention and is advantageous whenever an area located around an expected optical break-through is to be scanned. It is therefore preferred to use a scanning device to scan the tissue.

In a fifth embodiment of the invention, a tissue can be diagnosed as well as three-dimensionally measured and also treated, if it is tissue intended for treatment. For this purpose, there is provided a method of measuring a transparent or semi-transparent tissue, wherein illumination laser radiation is focused in a focal point and the position of the focal point within the tissue is changed, to which end a variable deflection of the illumination laser radiation is effected, and wherein tissue-specific signals induced by said focusing are detected and assigned to points of measurement whose location in the tissue is respectively defined by the determined position of the focal point, and wherein points of measurement are filtered out, thus allowing to determine the positions of boundaries and/or inclusions in the tissue.

This method can be realized in a particularly advantageous manner using a device for measuring a transparent or semi-transparent tissue, said device comprising a source of laser radiation, a deflecting unit, a focusing unit and a detector unit as well as a control unit, which controls the source of laser radiation, the deflecting unit and the focusing unit such that illumination laser radiation emitted by the source of laser radiation is sequentially focused in a plurality of focal points within the tissue by means of the deflecting unit and the focusing unit, said detector unit emitting tissue-specific signals, which are induced by said focusing, to the control unit, and said control unit assigns said signals to points of measurement whose location in the tissue is respectively defined by the position of the focal point, and filters out points of measurement and thus determines positions of boundaries and/or inclusions in the tissue.

Particularly advantageously, target points for a subsequent treatment of the tissue by means of treating laser radiation focused in the tissue can be obtained from the filtered-out points of measurement. In this connection, raster-scanning of a continuous three-dimensional area in the tissue advantageously allows to generate a complete model of the volume and to know, in particular, the position of boundaries and inclusions. Depending on the specific individual case, it sometimes also may be sufficient to scan the tissue only in a two-dimensional or even one-dimensional manner so as to obtain information required in order to generate target points for the action of treating laser radiation. The positional information of the filtered points of measurement thus provides the control unit with an optimal regime for focusing to the target points. The treating laser beam can then be moved within a short time on an advantageous line between the target points. This also allows to effectively avoid injuries to tissue which is not to be affected; nevertheless, a site to be treated may be located very close to sensitive parts of tissue, because the points of measurement allow an exact analysis. As to the position of the points of measurement relative to the target points, it may be advantageous, in the interest of quick measuring of the tissue to select the points of measurement to have a different step spacing than the target points, for example a greater step spacing. Target points are then also positioned between points of measurement, because it is advantageous to focus more target points than there are points of measurement that have been detected.

Since the localization of the focus of the illumination laser radiation in the points of measurement is effected by suitable control of the focusing unit (position of the point of measurement in the depth of the tissue) and of the deflecting unit (lateral position of the point of measurement), each point of measurement can be assigned to an unambiguous adjustment of the focusing unit and of the deflecting unit. The spatial position of the target point is thus also defined by suitable parameters of the focusing unit and of the deflecting unit. In order to achieve high precision here, a tolerance chain, which is sometimes inevitable when using two separate systems, is advantageously excluded by varying the treating laser radiation locally in the tissue by the same optical means by which the position of the focal point of the illumination laser radiation is also influenced. The thus achievable absolute precision in placing the focus of the treating laser radiation allows applications that were previously not possible because of the danger of inadvertently affecting closely adjacent, sensitive tissue.

Therefore, the treating laser radiation focused into the tissue preferably also acts as a measurement beam while being formed and guided by the same deflecting unit and the same focusing unit. The measurement and diagnosis as well as the treatment is thus conducted using the same laser beam which, coming from the same source of laser radiation, is focused in the tissue by the same optical means. This has the effect that detected points of measurement with reference to the optical break-throughs and desired target points are related to the same reference point as the target points. For the measurement, the power of the treating laser radiation is reduced, e.g. by optical means, so that it causes laser-induced signals in its focus which allow a measurement, but do not affect the tissue. To do so, it is advantageous to provide an energy reducer, which can be switched into the optical path of the treating laser beam and reduces the energy of the treating laser radiation focused in the tissue such that no irreversible change occurs in the tissue, but an induced signal is caused, which signal depends on the condition or type of the tissue and is accordingly detected in the detection beam path.

In this case, the measured points need not be identical with those points at which an optical break-through is generated. However, in this fifth embodiment, all of said points have a common reference base, because they are generated by the same optical path, coming from the same source of radiation. A tolerance chain, such as that potentially occurring when separate systems are used, is avoided.

For said measurement, the energy of the treating laser radiation, e.g. the energy of the individual laser pulses, is reduced by means of the energy reducer to such an extent that no irreversible changes in the tissue are created in the focal point. Alternatively, use can also be made of a property of a pulsed source of treating laser radiation to emit background radiation of strongly reduced power between the individual laser pulses. This background radiation can be used for measurement, and an energy reducer can be dispensed with.

The signals detected by the detection beam path are assigned to points of measurement which are respectively defined by the specific position of the detection beam path, e.g. by the specific position of a focusing unit and/or deflecting unit. These signals may be stored in a memory and may be compared with a threshold value in a subsequent comparator, said threshold value being fixed or being selectable as a function of the position of the individual points of measurement. This makes it possible to determine all those points of measurement for which treatment is to be provided. The corresponding positional information is transmitted to a control unit which determines a corresponding course of the generation of optical break-throughs. The treating laser radiation is then moved with its focus along a corresponding path. This allows to effectively avoid injuries to tissue which is not to be acted upon, even if a site to be treated is very close to parts of tissue that have to remain uninjured. The precision achievable is in the order of magnitude of the focus diameter and may even be below 1 µm, depending on the focusing and on the radiation wavelength. In order to generate the optical break-throughs the reduction of energy is terminated.

In the device of the fifth embodiment, a measurement step with the energy reducer switched on can be conducted on the path already traveled in order to generate the optical break-throughs, after generation of the optical break-throughs, in which step the optical break-throughs or their effect, respectively, are measured. Again, a comparison with the signals detected during the first measurement and stored in the memory is possible here. Depending on the result of said comparison to single or several points treating laser radiation can be applied again to arrive at a treatment which is as successful and as gentle as possible, i.e. a second treatment step is conducted. Thus, the number of steps can be freely selected within a sequence of measurement and treatment steps. It is therefore preferred to repeatedly determine points of measurement and target points, with treating laser radiation being respectively applied to the target points.

BRIEF DESCRIPTION OF THE DRAWINGS

The invention will be explained in more detail below, by way of example and with reference to the Figures, wherein:

FIG. 13 shows a functional connection between the displacement of the focus and the wavelength in the embodiment of FIG. 11;

FIG. 14 shows a further embodiment of the laser surgical instrument of FIG. 1;

DETAILED DESCRIPTION OF THE INVENTION

Figure 1:
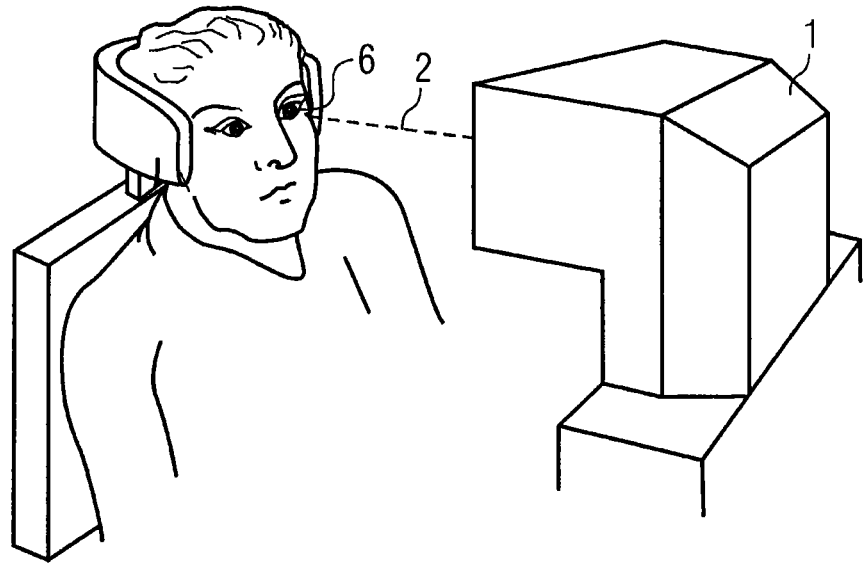
FIG. 1 shows a perspective view of a patient during a laser surgical treatment using a laser surgical instrument.

FIG. 1 shows a laser surgical instrument 1, which emits a treatment beam 2 being directed onto the eye 6 of a patient. The laser surgical instrument 1 is able to generate a pulsed treatment beam 2 such that the method described in U.S. Pat. No. 6,110,166 can be carried out. The pulse width is in the nanosecond or femtosecond range.

A visual deficiency in the eye 6 of the patient is remedied by means of the laser surgical instrument 1 by removing material from the cornea of the eye 6 so as to change the refractive characteristics of the cornea by a desired extent. In doing so, the material is removed from the stroma of the cornea. The stroma is located beneath the epithelium and Bowman's membrane and above Decemet's membrane and the endothelium.

The material removal is effected by separating layers of tissue in the stroma by focusing the high-energy pulsed treatment beam 2 of the laser surgical instrument 1. In this case, each individual optical break-through initiates a plasma bubble, so that the separation of tissue layers covers a larger area than the focus of the treatment beam 2. By suitable deflection of the treatment beam 2, plasma bubbles are lined up during treatment. The lined-up plasma bubbles circumscribe a partial volume of the stroma: the material to be removed.

Due to the treatment beam 2, the laser surgical instrument 1 operates in the manner of a surgical knife which, without affecting the surface of the cornea, cuts material directly inside the stroma. If the cut is guided to the surface of the cornea by generating further plasma bubbles, the material of the stroma isolated by the cutting path can be laterally pulled out of the cornea and thus removed.

The cut performed by the laser surgical instrument 1 is guided according to predetermined parameters, so that the removed partial volume of the stroma causes such a change in the optical properties of the cornea that a previously existing visual deficiency is corrected to the greatest possible extent.

In order to monitor the precision of the cutting path, the laser surgical instrument 1 is provided with a measurement device which detects the spatial extents and/or the positions of the plasma bubbles generated by the treatment beam 2 in the corneal tissue of the eye. The measurement allows optimum control of the treatment beam 2. Said control may affect both the scanning movement of the treatment beam 2 and the control of the beam parameters of the treatment beam 2 with regard to the generation of the optical break-through. The diameter of the plasma bubbles generated is of great importance in guiding the laser beam during the scanning operation, because the distance between individual plasma bubble centers should not exceed the average plasma bubble diameter. Otherwise, there would be a gap in the line of plasma bubbles, i.e. there would still remain continuous tissue between the disrupted volumes. Isolation of stroma material to be removed would then be possible only with great difficulty or even not at all. In any case, the optical result would be unsatisfactory.

However, optimizing the parameters of the treatment beam 2 also allows to keep the plasma bubbles as small as possible. The smaller the plasma bubbles are, the finer will be the cut formed by the laser surgical instrument 1. This is important, in particular, if it is taken into consideration that usually lens-shaped partial volumes are to be removed from the stroma. The precision of the cutting path and the fineness of the cut are particularly important at the edges of such lens-shaped volumes.

The measured values of the measurement device may either be transformed into a display on the laser surgical instrument 1, which allows to check the parameters of the treatment beam 2 or the guidance of the treatment beam 2 as to whether desired and pre-defined values are actually present. As an alternative, it is possible to effect closed-loop control of the parameters of the treatment beam 2 or of the deflection of the treatment beam 2 by means of an automatic process control to obtain certain values. Such laser surgical instrument 1 works fully automatically.

Figure 2:
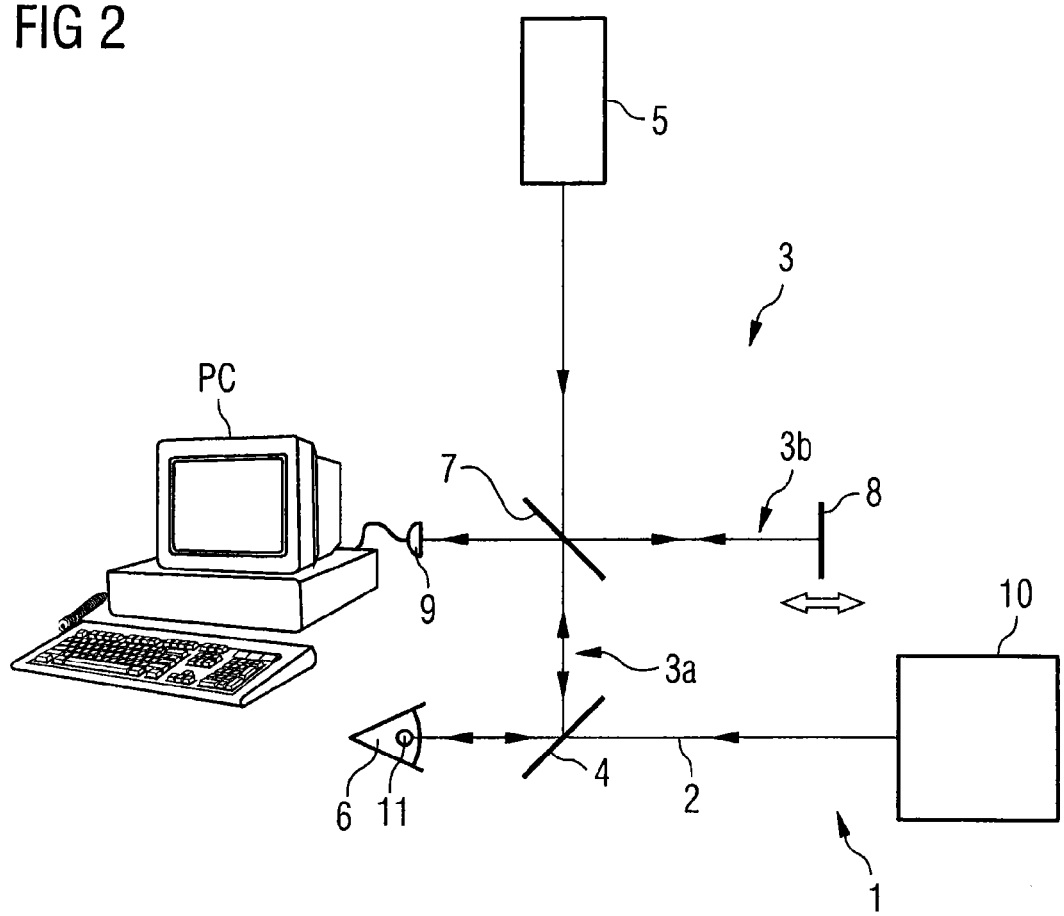
FIG. 2 shows a schematic representation of the laser surgical instrument of FIG. 1.

FIG. 2 shows a first embodiment of the laser surgical instrument 1. The measurement device is realized here as an optical coherence tomograph 3 and follows the principle described in the publication Arch. Ophtalmol., Vol. 112, p. 1584, "Micrometer-scale Resolution Imaging of the Interior Eye in vivo with Optical Coherence Tomography" by J. Izatt et al.

The optical coherence tomograph 3 is integrated into the treatment beam 2 of the laser surgical instrument 1 via a coupling-in beam splitter 4 and comprises a measuring arm 3a as well as a reference arm 3b. The coupling-in beam splitter 4 couples radiation from a measuring laser 5 into the light path of the laser surgical instrument 1 such that the optical axes of the treatment beam and of the measurement laser beam coincide. The focus of the treatment beam 2 and the focus of the radiation of the measurement laser 5 are located in approximately the same position laterally (not visible in FIG. 2). Both foci are formed in the cornea of the eye 6 by focusing optics 13 arranged following the coupling-in beam splitter 4.

Figure 3:
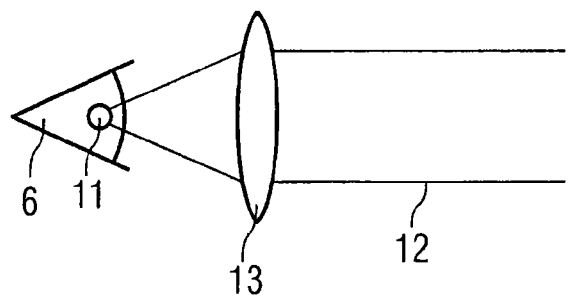
FIG. 3 shows the focusing of a beam onto the eye of the patient in the instrument of FIG. 2.

FIG. 3 shows how the already combined radiation of the measurement laser 5 and of the treatment beam 2 is focused into the cornea of the eye 6 as an incident beam 12 by means of the focusing optics 13. If the energy density of the treatment beam 2 (pulse length and radiation power) is above a certain threshold value, an optical break-through appears in the focus, creating a plasma bubble 11.

The radiation of the measurement laser 5 is scattered back at the plasma bubble 11, coupled out again at the dichroic coupling-in beam splitter 4 and then passes to a measurement beam splitter 7, where it is superimposed on radiation from the measurement laser 5, which was previously split off by a measurement beam splitter 7 toward a mirror 8. The position of the mirror 8 is adjustable. Thus, the measuring arm 3a extends from the measurement beam splitter 7 through the coupling-in beam splitter 4 to the eye 6, and the reference arm 3b is formed between the measurement beam splitter 7 and the adjustable mirror 8.

The radiation returning from the reference arm 3b and from the measuring arm 3a to the measurement beam splitter 7 is brought to interference on a photo receiver 9. Since the measurement laser 5 of use is a light source which exhibits a relatively short axial coherence length (temporal coherence length) of about 10 μm in combination with a high spatial coherence, an interference pattern appears on the photodiode 9 only if the optical lengths of the measurement arm 3a and of the reference arm 3b differ by not more than the temporal coherence length of the radiation from the measurement laser 5. In order to achieve a maximum in resolution using the optical coherence tomograph 3, a measurement laser 5 having a minimal temporal coherence length, which is below 10 μm in the embodiment example, is used.

In order to prevent any influence of the treatment beam 2 of the laser surgical instrument 1, which is emitted by a treating laser 10 and is directed onto the eye 6, on the optical coherence tomograph, the wavelength region of the radiation from the measurement laser 5 differs from the wavelength region of the observation radiation 2, and the coupling-in beam splitter 4 has suitable dichroic properties. For example, a measurement laser 5 is used which emits radiation at approximately 850 nm with a bandwidth as large as possible. A large bandwidth promotes axial resolution, because the bandwidth is inversely proportional to the temporal coherence length of light. When using different wavelengths for the radiation of the measurement laser 5 and the observation beam 2, superposition and separation of the beams may be effected using a dichroic coupling-in beam splitter 4. Additionally or alternatively, suitable filters may be employed in the beam path of the optical coherence tomograph.

In order to measure the location of a plasma bubble 11, the mirror 8 is displaced until an interference pattern appears on the photodiode 9. If the signal from the photodiode 9 which is read out by a computer PC indicates interference of the radiations from the measuring arm 3a and from the reference arm 3b, the measuring arm 3a and the reference arm 3b have equal length, and the distance from the focus of the radiation from the illumination laser 5 in the cornea of the eye 11 is known. The accuracy of measurement is the temporal coherence length of the radiation of the measurement laser 5, i.e. the coherence length in the propagation direction.

The back-scattering of radiation of the measurement laser 5 at the eye 6 provides an indication of the discontinuities in refractive index in the cornea of the eye 6, which occur both at the boundary of different tissues, e.g. between the stroma and the Bowman's membrane, and at the site of interaction between the treatment beam 2 and the cornea of the eye 6, both below and above a threshold at which the above-mentioned optical break-through occurs with photo disruption and/or photo ablation.

In order to allow a maximum axial area to be measured, a device for changing the divergence of the radiation of the measurement laser 5 (not shown in FIG. 2 for simplification) is provided between the measurement beam splitter 7 and the coupling-in beam splitter 4, in addition to a long stroke for the mirror 8, so that the divergence of the radiation coming from the measurement laser 5 can be adjusted before coupling into the treatment beam 2. The focusing optics 13 arranged following the coupling-in beam splitter 4 then effect focusing of the measurement beam 2 and of the radiation coming from the measurement laser 5 into different focal points, wherein the adjustment of the device affecting the divergence of the radiation coming from the measurement laser 5 allows to adjust the focus position of the radiation from the measurement laser 5, independently of the focus of the treatment beam 2. Thus, the focus of the observation radiation is adjustable along the optical axis relative to the focus of the treatment radiation 2. Thus, back-scattered radiation also becomes detectable along the optical axis of the treatment beam 2 in an area which is greater than the stroke of the mirror 8.

The device for adjusting the divergence of the measurement laser 5 further allows to design the spot size of the focused radiation of the measurement laser 5 to be approximately as large as the spot size of the focused observation beam, because scanning in an axial direction, i.e. along the axis of the observation beam 2, is then achieved by synchronous adjustment of the divergence-changing device and the mirror 8. Due to the relatively narrower focusing of the radiation of the measurement laser 5 in this variant, the coherence tomograph 3 thus provides an axial resolution which is even better than the temporal coherence length of the radiation from the measurement beam 5. The precision of measurement accordingly increases. If this is not required, the device influencing divergence can be omitted between the coupling-in beam splitter 4 and the measurement beam splitter 7. Axial displacement of the area from which back-scattered radiation may lead to interference on the photo receiver, is then effected exclusively by adjusting the mirror 8, and axial resolution is mainly determined by the coherence length of the measurement laser 5 (typically in the order of magnitude of 10 μm).

Figure 4:
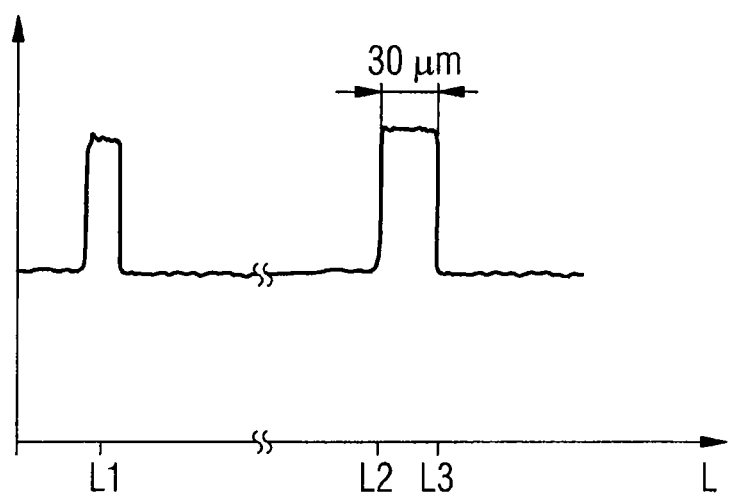
FIG. 4 shows a signal course during measurement of scattering centers which are generated during the laser surgical treatment in the eye.

FIG. 4 shows a signal obtained with a laser surgical instrument 1 which comprises an optical coherence tomograph 3 of the construction shown in FIG. 2. The signal is plotted here as a function of the adjustment of the mirror 8, with the stroke L of the mirror 8 being indicated as a variable in FIG. 4. The signal is derived from the interference phenomenon detected by the photo receiver and has been generated by the computer PC. The signal encodes the depth of modulation of said interference and has a high level whenever the signal of the photo receiver 9 indicates an interference phenomenon.

As FIG. 4 shows, a first interference appears at a displacement L1. Said interference is caused by radiation scattered back at the epithelium of the cornea. With a further displacement of the mirror 8, a second peak of the signal appears at a displacement L2. This interference is caused by the discontinuity in the refractive index at the plasma bubble 11. Said interference lasts until a displacement L3 occurs. Although the size of the plasma bubble affects the distances L2, L3, the measurement resolution of the coherence tomograph 3 does not allow measurement of bubble diameters of approximately 30 µm or less. The use of a source of radiation having a shorter temporal coherence length enables such diameter measurement as well.

The distance between the displacement L1 assigned to the epithelium and the beginning of the interference peak at the displacement L2 indicates how far beneath the epithelium, i.e. the surface of the cornea, the plasma bubble is located. Thus, the position of the plasma bubble 11, caused by the treatment beam 2 in the cornea of the eye 6, can be detected from the signal in the form of the distance from the epithelium. As an alternative to referring to the epithelium, reference may be made, of course, to the endothelium. In this case, a new peak is to be expected, due to radiation scattered back at the endothelium, in the representation of FIG. 4, upon further displacement. Instead of the endothelium or the epithelium, a discontinuity in the refractive index at the Bowman's membrane or at the Decement's membrane may, of course, be used also as a reference.

The computer PC, which reads out the signal from the optical coherence tomograph 3, generates the signal. It further serves to control the treating laser 10, for which purpose it feeds a display which indicates the position of the plasma bubble 11 generated by the treatment beam 2. On the other hand, this axial position of the plasma bubble is evaluated to control the treatment beam 2 and is used to guarantee that the step of isolating the partial volume in the stroma is effected as desired.

In an embodiment which fully automatically monitors the observance of values pre-defined by treating surgeons, the computer controls parameters of the treatment beam 2. The surgical instrument then operates using on-line monitoring and on-line control.

Figure 6:
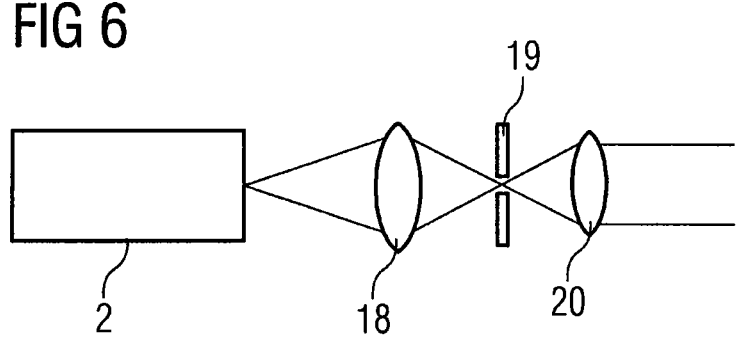
FIG. 6 shows a light source for the laser surgical instrument of FIG. 2.

The measurement laser 5 has the structure shown in FIG. 6. It consists of a laser 2 as well as a subsequently arranged beam-forming unit comprising a lens 18, a stop 19 and a further lens 20. The beam diameter thus generated is adapted to the beam diameter of the treatment beam 2. By adjusting the lenses 18 and 20, the beam diameter may be additionally reduced or enlarged in order to adjust the range of resolution or measurement. In addition, divergence may be changed by adjusting the lens 20, thus allowing the focus position of the measurement beam to be set.

Figure 5:
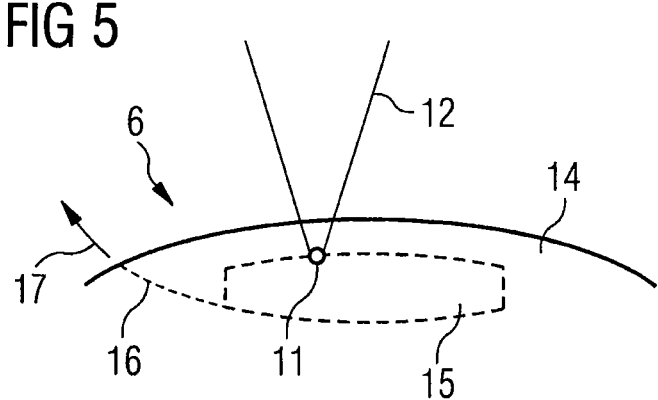
FIG. 5 shows a schematic representation explaining a cutting path during the laser surgical treatment.
Figure 7:
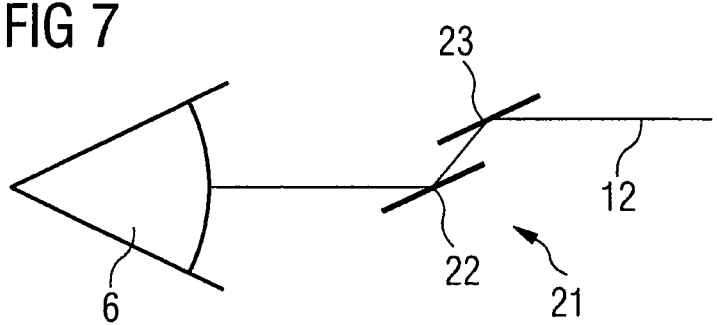
FIG. 7 shows a scanning device for the laser surgical instrument of FIG. 1.

In a schematic representation, FIG. 5 shows the cut executed by the surgical instrument 1 under on-line control. The incident beam 12 is focused into the cornea 14 of the eye 6 by the focusing optics 13. As already explained, the plasma bubble 11, which is generated by a pulse of the treatment beam 2, acts as a surgical knife which separates layers of tissue inside the cornea 14. By adjusting the incident beam 12 by means of a scanning unit 21, which is shown in FIG. 7 and comprises scanner mirrors 22, 23 being rotatable about orthogonal axes, a plurality of plasma bubbles are placed next to each other, and a lenslet 15 is circumscribed, which is thus cut out of the stroma of the cornea 14. A possible form of cut which may achieve this is shown in U.S. Pat. No. 6,110,166, which describes a spiral-shaped line-up of plasma bubbles 14.

After such cut around the lenslet 15, a lateral cut 16 is performed, which allows to remove the now isolated lenslet 15 from the cornea 14 along the direction 17. The cutting path has the advantage that, in the central area of vision, in which the optical correction is effected by removal of the lenslet 15, there is no cut leading through the endothelium to the outside. Instead, said lateral cut 16 is located at the optically less important periphery of the cornea 14.

The scanning unit 21 shown in FIG. 7 serves to adjust the incident beam 12. It comprises two scanning mirrors 22, 23, which are independently rotatable about two axes which are perpendicular to one another. Thus, the incident beam 12 can be guided across the cornea 14 in a two-dimensional manner. Axial adjustment of the incident beam 12 is effected by adjusting the focusing optics 13, i.e. by changing the position of the focal point in which the energy density required for an optical break-through, and thus the plasma bubble 11, is generated.

Figure 8:
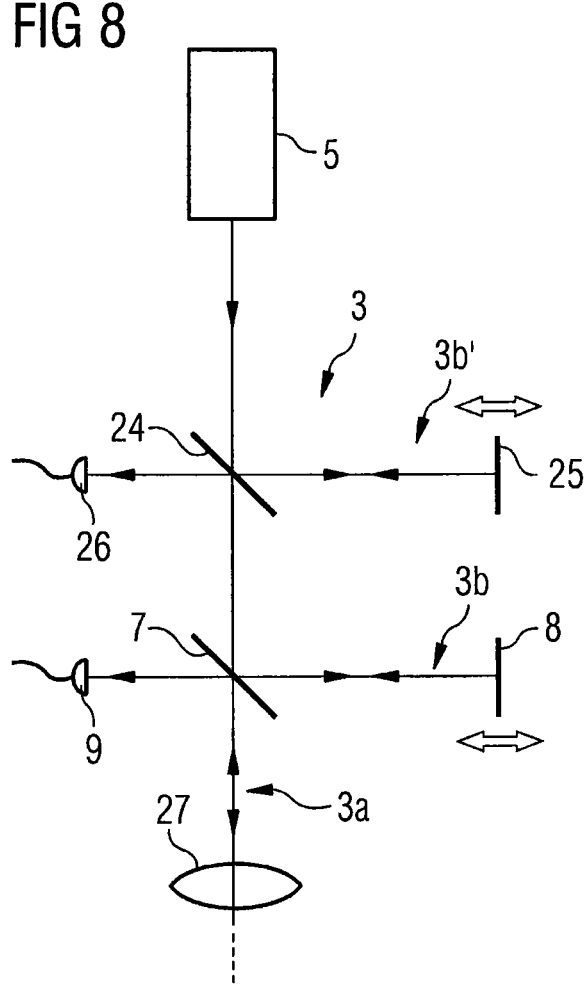
FIG. 8 shows a further embodiment of a measurement device of the laser surgical instrument of FIG. 1.

In order to precisely determine the axial position of the generated plasma bubble, the mirror 8 of the optical coherence tomograph 3 is adjusted as described with reference to the signal shown in FIG. 4. This may be effected, for example, by an oscillation which passes through the area between positions L1 and L2 each time. In the case of a measurement device having high axial resolution, such a great adjustment of the mirror 8 may, however, be mechanically very complex or time-consuming in some cases. For such cases, the construction of the optical coherence tomograph 3 schematically shown in FIG. 8 is provided, which comprises several, e.g. two, reference arms 3b and 3b' that are substantially similar to each other, i.e. they have an adjustable mirror 8 (reference arm 3b) and 25 (reference arm 3b'), respectively. Each reference arm 3b, 3b' is associated with a photo receiver 9, 26.

The length of the reference arm 3b can be set independently of the length of the reference arm 3b'. Thus, radiation scattered back with high resolution simultaneously at the plasma bubble and at the epithelium can be measured, for example, by adjusting the reference arm 3b' to the reflection to a reference surface, i.e. the epithelium, and reference arm 3b detecting the boundary of the plasma bubble.

Moreover, FIG. 8 shows a possible construction of the device for changing the divergence of the radiation from the measurement laser 5, which device was already mentioned with reference to FIG. 2, but not shown therein. The coherence tomograph of FIG. 8 is provided with an adjustable zoom optics 27.

The optical coherence tomograph 3 as used in the constructions according to FIG. 2 or 8 provides for a spatial selection of the area from which back-scattered radiation is recorded. Axial selection is effected by the interferometer construction comprising the measuring arm 3a and the reference arm 3b (or additional pairs thereof). The focusing optics 13 effect a lateral selection by focusing. The spatial selection is freely selectable, i.e. independently of the position of the treatment beam focus, if the optical coherence tomograph is provided with an independent scanning unit similar to FIG. 7. Then the area around an optical break-through or a plasma bubble 11 can be scanned at higher resolution. The zoom optics 27 allow sensing of the area around the plasma bubble 11 not only laterally, i.e. transversely of the optical axis of the treatment beam 2, but also axially along said optical axis, in a large measurement range.

Figure 9:
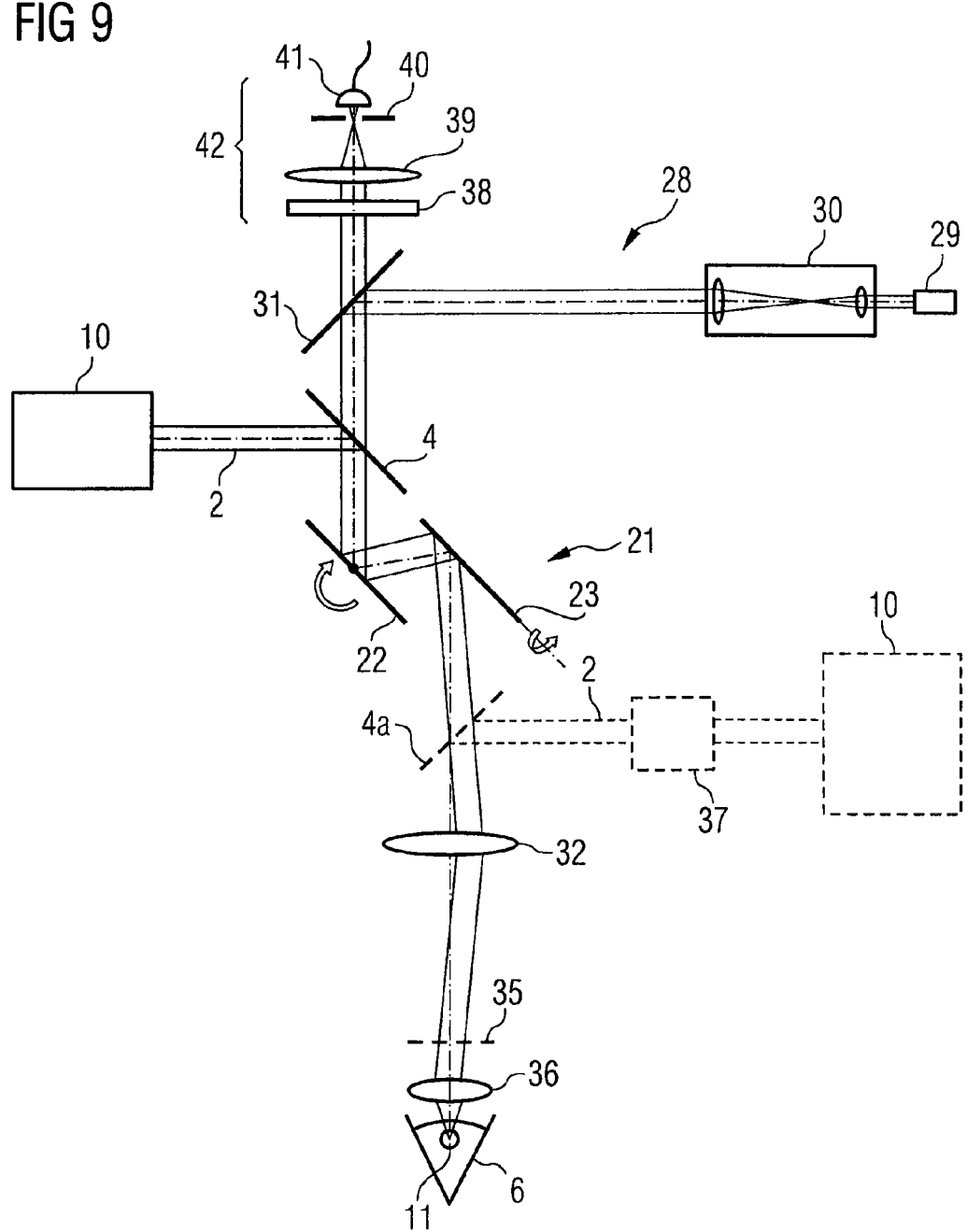
FIG. 9 shows a schematic representation of a further embodiment of the laser surgical instrument of FIG. 1.

FIG. 9 shows a second embodiment of the laser surgical instrument 1. The basic principle here is to detect radiation having a large and adjustable depth of focus, which radiation is scattered back by suitable spatial filtering at the eye 6 and, in particular, at a plasma bubble 11 generated there, in a manner allowing measurement of at least the axial extent of a scattering structure in the cornea of the eye, for example of the plasma bubble 11 generated by the optical break-through. For this purpose, a confocal microscope 28 is provided, which operates in the manner of a laser scanning microscope.

The confocal microscope 28 is provided with a laser 29 whose radiation is adapted by an optical arrangement 30 with regard to beam parameters, such as the position of necking at the focus and the beam cross-section. The illumination radiation thus obtained is passed to a scanning unit 21 by means of a splitter 31, said scanning unit comprising two scanning mirrors 22 and 23 like the scanning unit of the previous constructions. The scanning mirrors 22 and 23 are arranged closely adjacent and in immediate proximity to a pupil of the beam path. As shown in FIG. 9, the mirrors have rotary axes that are perpendicular to each other, and they may be separately controlled. For each beam deflection which depends on the actuation of the scanning unit 21, radiation is collected by scanning optics 32 in an aperture plane 35, from where an objective 36 generates a spot image which is located in an object plane situated in the eye 6. The treatment beam 2 is also effective in the area of this object plane. As in the previous embodiments, the treatment beam 2 comes from a treating laser 10 and is combined with the beam path of the confocal microscope via a coupling-in beam splitter 4.

Radiation scattered back in the object plane, e.g. at a plasma bubble 11, passes back to the beam splitter 31 via the described optical path. The radiation of the sensed volume element and coming from the object plane, i.e. radiation scattered back at the eye 6, is detected in a detecting arm 42 after having passed through the beam splitter 31. Depending on the design of the beam splitter 31, the radiation is guided, at least partially, or, in the case of a dichroic design of the beam splitter 31, almost completely, to an interference filter 38 and to a lens 39, by which a spot image of the back-scattering object in the object plane is generated in a pinhole plane in which a pinhole aperture 40 is located. The pinhole aperture 40 is followed by a photo multiplier 41 which provides a signal that is transformed into an image signal by an evaluating unit (not shown) connected thereto, which unit considers the current position of the scanning unit 21.

The size of the pinhole aperture sets the size of the object structure to be detected in the object plane. Even more decisive is, however, that a decreasing diameter of the pinhole aperture leads to an enhanced depth discrimination in the object plane, i.e. the size of the pinhole aperture determines from which axial area around the object plane radiation can reach the photo multiplier.

The confocal method used in the confocal microscope 28 allows to direct radiation from a selected volume element in the object under examination to the photo multiplier 41 and to almost completely suppress radiation emitted by other volume elements. In particular, radiation from tissue layers located further down or higher up is blocked out.

The pinhole aperture 40 and the object plane from which radiation is detected are located in conjugated planes. Adjustment of these planes, for example by adjusting the lens 39, makes it possible to effect an axial depth scan such that the object plane from which radiation reaches the photo multiplier 41 is adjusted. Said adjustment is required, for example, in order to measure a plasma bubble 11 in an axial direction, i.e. along the axis on which the treatment beam 2 is incident.

Increased independence between the axial position of the aforementioned object plane and the focal point of the treatment beam 2 may be achieved by arranging the divergence-changing device already mentioned with respect to the constructions according to FIGS. 2 and 8, e.g. in the form of zoom optics, such that it precedes the coupling-in of the treatment beam 2 via the coupling-in beam splitter 4. Suitable adjustment of this device then allows the object plane to be adjusted virtually freely relative to the focal plane of the treatment beam 2.

In the construction shown in FIG. 9, a single scanning unit 21 is provided for structural simplification, said scanning unit 21 synchronously changing the lateral position of the spot image, from which reflected radiation is passed to the photo multiplier 41, as well as the focal point of the treatment beam 2. It is not possible to laterally displace the spot within the object plane relative to the focal point of the treatment beam 2.

Use of two independent scanning units avoids this limitation. The illumination and detection beam path of the confocal microscope 28 can then be independently adjusted relative to the treatment beam 2 at the eye 6. Such a construction is indicated in broken lines in FIG. 9. The coupling-in beam splitter 4 is then replaced by a coupling-in beam splitter 4*a* which is arranged following the scanning unit 21 of the confocal microscope 28 in the direction of illumination. Here, the treating laser 10 is provided with its own treatment scanner 37, which is operable independently of the scanning unit 21 of the confocal microscope 28. This more complex construction allows the confocal microscope 28 to record radiation from the eye 6 at points which may be selected completely independently of the focus position of the treatment beam 2 and thus completely independently of the generation of the plasma bubbles 11. This allows not only to determine the axial extent of a plasma bubble 11, but also to measure lateral dimensions.

In the construction of the measurement device of the laser surgical instrument 1 shown in FIG. 9, separate observation radiation is generated by means of the laser 29, the optical arrangement 30 and the coupling-in mirror 31. For some applications, this may be dispensed with, and just a confocal detection of scattered light coming from the treatment beam 2 at the eye 6 may be effected. In addition, a phase-sensitive detection, e.g. according to the Nomarski method, may be applied as described in the publication by Padawer J., "The Nomarski interference-contrast microscope. An experimental basis for image interpretation." J. Royal Microscopial Society (1967), 88, pp. 305-349, whose disclosure is explicitly incorporated by reference herein.

In the construction of FIG. 9, particularly good sensitivity is achieved, if the coupling-in beam splitter 4 or 4*a*, respectively, is dichroic, i.e. if it has a beam-deflecting effect essentially only for the wavelengths of the treatment beam 2. This dichroic property is also advantageous for the variant without separate illumination radiation, because it has been shown that in plasma bubbles 11 broad-band radiation is generated also outside the spectral range of the treatment beam 2.

The confocal detection method is usually effected using optics which are chromatically corrected to the best possible extent. This ensures that the radiation from a specific volume element arrives at the detector, e.g. the photo multiplier 41, in a wavelength-independent manner.

Figure 10:
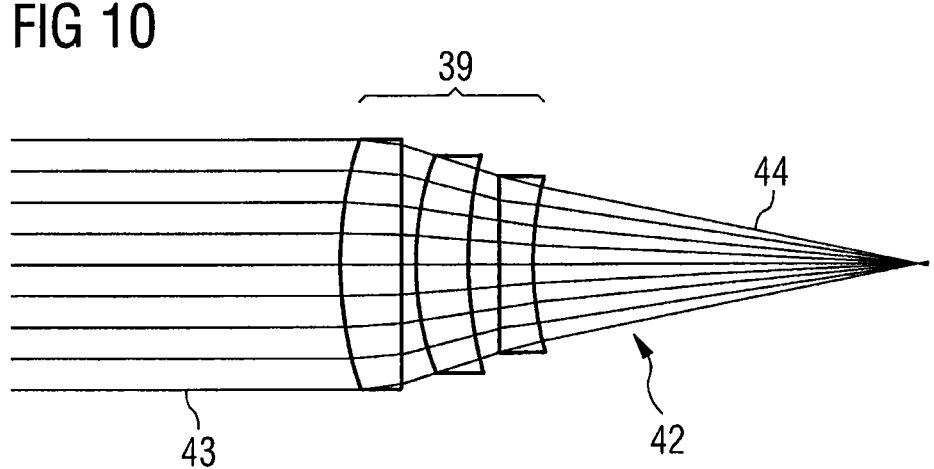
FIG. 10 shows a beam path in the region of the focus of treating laser radiation from the laser surgical instrument acting on the eye.

In contrast thereto, according to a third embodiment modifying the second embodiment, the optics which project light from the objective onto the pinhole aperture 40 are deliberately designed to be dispersive. In this connection, FIG. 10 shows an enlarged view of the detecting arm 42 of the confocal microscope 28.

Figure 11:
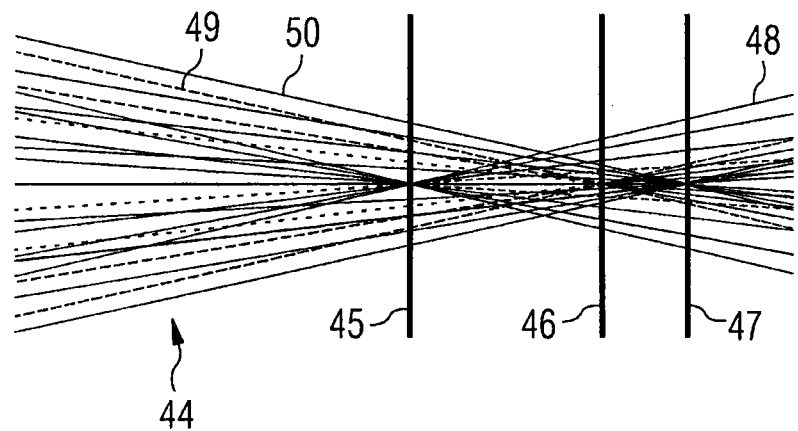
FIG. 11 shows a schematic representation of focus positions in a further embodiment of a measurement device for the laser surgical instrument of FIG. 1.

An incident detection beam 43 is transformed by the lens 39, which is now provided as a multi-component lens, into a focused detection beam 44. Due to dispersive, i.e. wavelength-dependent, focusing properties of the optical group forming the lens 39, the effective focal length for light in the blue spectral region is clearly shorter than for light in the red spectral region. Thus, white light, which consists of red, green and blue spectral components and is emitted by a volume element, is focused into different foci, as shown by way of example in FIG. 11. The blue radiation 48 is focused into a focal plane 45, which is located in front of a focal plane 46 for green radiation, which is in turn followed by a focal plane 47 for red radiation 50.

Figure 12:
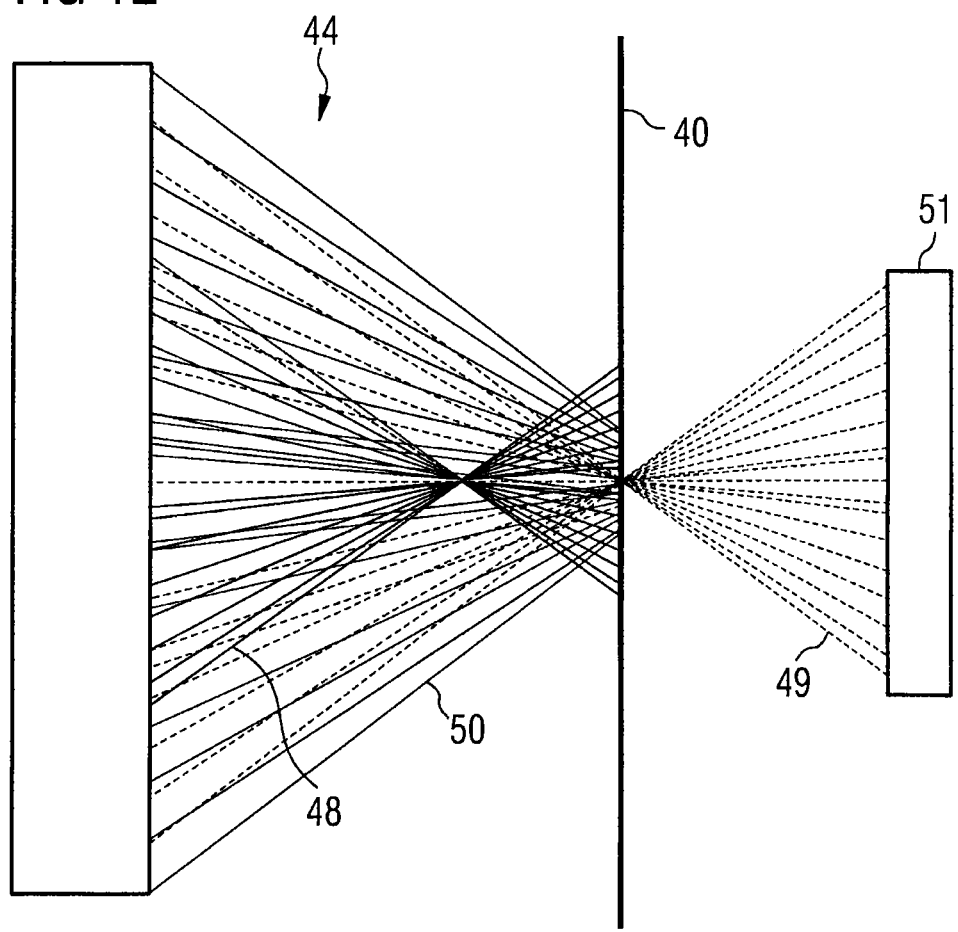
FIG. 12 shows a detailed representation of the radiation directed onto a detector of the embodiment according to FIG. 11 with a pinhole.

The dispersive properties of the lens 39 are utilized for spectrally selecting depth information or for obtaining further depth information. As shown in FIG. 12, for a given volume element, the dispersive optics of the lens 39 focus only green spectral components precisely in the pinhole aperture 40, because only for these spectral components is the focal plane 46 located in the plane of the pinhole aperture 40. The focus of the blue radiation 48 is located on the optical axis in front of the plane of the pinhole aperture 40, so that the blue radiation diverges again on the way between its focal plane 45 and the plane of the pinhole aperture 40. Thus, only a small, almost unnoticeable part of blue radiation 48 is transmitted through the pinhole aperture 40, resulting in effective suppression of the blue radiation 48 coming from the given volume element. This likewise applies for the red radiation 50, because the focal plane 47 thereof is located behind the plane of the pinhole aperture 40; the red radiation from the volume element is thus also blocked by the pinhole aperture 40. In conclusion, in the schematic representation of FIG. 12, only green radiation 49 of the volume element reaches the detector, which is provided as a spectrometer 51 here.

Referring now to a further white-light radiating volume element, which is located on the optical axis between the previously considered volume element and the optics, the green component thereof is now focused in a plane behind the plane of the pinhole aperture 40. However, the blue radiation from this further volume element has a focus in the pinhole aperture, if the axial distance of both volume elements corresponds exactly to the focus displacement, with the magnification of the optical projection having to be taken into consideration as well. The same applies to a volume element, which, as seen from the objective, is accordingly located behind the first explained volume element. From this third volume element, only red components of the radiation can pass through the pinhole aperture 40. Thus, a spectral radiation mixture passes through the pinhole aperture 40, wherein the spectral information encodes the axial position of the volume element emitting said radiation.

The spectral analysis of the radiation passing through the pinhole aperture 40 by means of the spectrometer 51, therefore, provides axial resolution, without having to adjust the confocal microscope. The spectral information carries depth information about the volume element, from which the radiation of the spectral region comes. The axial position of the volume element, from which the radiation of the spectral channel originates, is determined from the relative height of individual spectral channels. In the simplest case, an evaluation using two or three channels will suffice.

Further, the size of a radiating volume element is determined in this approach. In a three-channel spectral analysis a small radiating volume element will generate, in only one channel, a signal exceeding a certain threshold value. For a medium-sized volume, two signals may also indicate a corresponding signal, but never all three channels, as long as the volume element is smaller than the focus offset between those channels that are spectrally the furthest apart. If there is a large radiating volume element, however, the spectrometer will essentially provide approximately equal signals in all channels. The width of the spectral distribution, which is indicated by the spectrometer 51, thus bears information on the size of the volume element. The wider the spectral distribution is, the larger is the volume element.

The focus offset dF achieved by the dispersive optical group of the lens 39 is plotted in FIG. 13 as a function of the wavelength LAMBDA, with all values being indicated in µm. For a spectral region from blue to red, there will be a focus displacement in the order of magnitude of at least 1 mm.

Thus, the use of the aforementioned spectrally selectively detecting confocal microscope 28 allows detection of plasma bubbles having a maximum extent of up to 1 mm. Since this range of measurement usually suffices, the third embodiment can also dispense with an axial adjustment of the object plane of the confocal microscope and still provide information on the axial extent of a plasma bubble 11 sufficient for on-line control.

Of course, the spectral distribution of the radiation coming from the examined object also plays a role here. The spectral detection of confocally recorded radiation when using dispersive optics requires that radiation having a certain broad-band spectral distribution be available from the object plane. In this case, in the simplest embodiment, the radiation of a plasma bubble 11 to be detected may be sensed directly, because the plasma emits, during the process of disruption which was initiated by the treatment beam 2, radiation having a broad spectrum. For certain applications, however, the spectral distribution of the radiation may have properties that are not sufficiently constant temporally or spectrally. For these cases, external illumination is provided. Said external illumination must have the required spectral bandwidth, e.g. a white-light LED or a light bulb can be used.

In a variant of the third embodiment, no spectrometer 41 is employed. Instead, illumination of the volume element to be detected or of the spot, respectively, is effected using spectrally controlled radiation. The radiation is spectrally adjusted in a sequential manner. In a simple construction, a blue, a green and a red LED are used for illumination, which are sequentially switched on. Information on the individual spectral channels is then obtained in a time-sequential manner, so that a suitable design of the source of illumination in this modification will allow working with an inexpensive detector which exhibits no, or otherwise only insufficient spectral discrimination properties.

FIG. 14 relates to a fourth embodiment of a laser surgical instrument 1. For the measurement device, it uses the principle of a slit lamp by irradiating illumination radiation on an optical axis which extends inclined to an optical axis along which observation takes place.

The measurement device is designed as a slit-lamp arrangement 52, which illuminates the cornea 14 of the patient's eye 6 in a slit-shaped manner. The slit optics 53 image a very narrow light bundle into the cornea, along an optical axis 60 of the slit illumination. Said light bundle may be generated, for example, using a slit or a part which serves as a controllable or programmable stop, such as a micromirror array or the like. In the construction of FIG. 14, a micromirror array is used, which is illuminated with radiation. Only one or few mirror lines reflect the light to the cornea 14. The slit illumination via the slit optics 53 may be adjusted with regard to the angle of incidence, i.e. with regard to the position of the optical axis 60, in a scanning unit 54, which is indicated by the bent double arrow in FIG. 14. This is effected by suitably controlling the micromirror array.

In the cornea, the input slit-shaped illumination is scattered at scattering centers, for example the epithelium, the endothelium, or plasma bubbles 11 generated by the laser surgical instrument 1. The scattered light is recorded by an objective 56, which also focuses the treatment beam 55 into the cornea 14. The treatment beam 55 of the laser surgical instrument 1 is coupled into the optical path via the coupling-in beam splitter 4 also in this embodiment. The coupling-in beam splitter 4 separates the scattered light recorded by the objective 56 and guides it to a photo receiver 59 by means of imaging optics 58. The objective 56, the coupling-in beam splitter 4 and the imaging optics 58 form an observation beam path.

The photo receiver 59 only records radiation which comes from the intersection point between the optical axis 60 of the slit illumination and the optical axis 61 of the selection or observation beam path. A scattered-light channel 57, from which scattered light resulting from the slit illumination is recorded, is defined at the intersection point.

By the scanning movement of the slit illumination, the scattered-light channel is displaced along the optical axis 61 of the detection beam path. A rotation of the optical axis 60 of the slit illumination to the left, in the representation of FIG. 14, displaces the scattered-light channel toward the endothelium, and a rotation to the right displaces it toward the epithelium. The rotation of the optical axis 60 of the slit-shaped illumination allows scanning of the cornea 14 along the optical axis 61, and the position of a plasma bubble 11 can be precisely determined by a scanning displacement of the scattered-light channel 57 from the endothelium to the epithelium. The bubble's position can be referenced by referencing to the reflections from the endothelium or the epithelium, respectively, or Bowman's membrane with regard to the distance therefrom, thus enabling not only determination of the diameter of the plasma bubble 11, but also (absolute) position detection relative to the endothelium and the epithelium.

Figure 15:
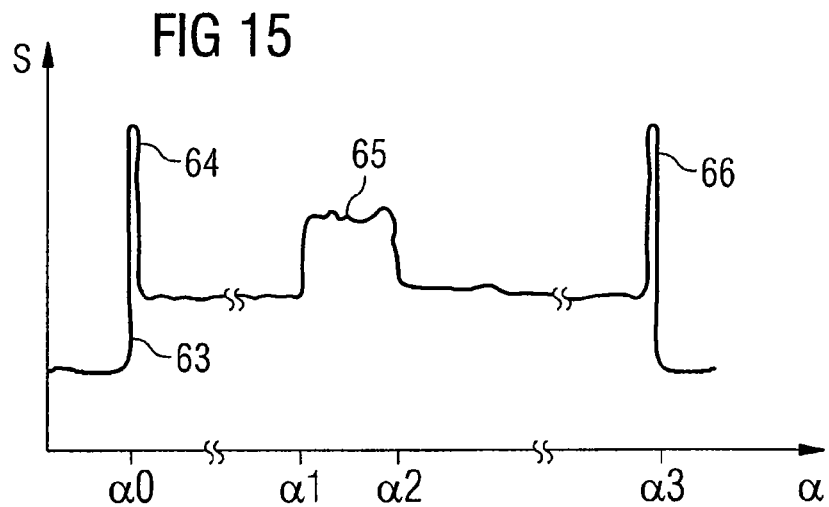
FIG. 15 shows a signal course as obtained with the embodiment of FIG. 14.

The signal obtained with the slit-lamp arrangement 52 is represented in FIG. 15, which shows the signal level, i.e. the radiation intensity registered by the photo receiver 59 in a signal course 63, plotted against a scanning angle $\alpha$ of the optical axis 60, along which the slit-shaped illumination is irradiated.

As can be seen, a first signal peak appears at an angle $\alpha 0$, said angle resulting from a reflection at the back-surface 64 of the cornea 14, i.e. from the reflection at the endothelium. A plasma bubble reflection 65, whose width is a measure of the extent of the plasma bubble 11 along the optical axis 61, is detected between angles $\alpha 1$ and $\alpha 2$. Finally, at the angle $\alpha 3$, a front-surface reflection coming from the endothelium is registered. The known thickness of the cornea 14 gauges the distance between the angles $\alpha 0$ and $\alpha 3$ as a measure of thickness, allowing to convert the distance between $\alpha 0$ and $\alpha 1$, i.e. the height of the plasma bubble above the endothelium, the distance between $\alpha 1$ and $\alpha 2$, i.e. the thickness of the plasma bubble, as well as the distance between $\alpha 2$ and $\alpha 3$, i.e. the depth of the plasma bubble beneath the epithelium, to a measure of length.

If lateral information is to be obtained, in addition to the axial information provided by the scanning movement of the slit-shaped illumination, imaging onto an imaging detector instead of the photo receiver 59 may be effected in the detection beam path.

Figure 16:
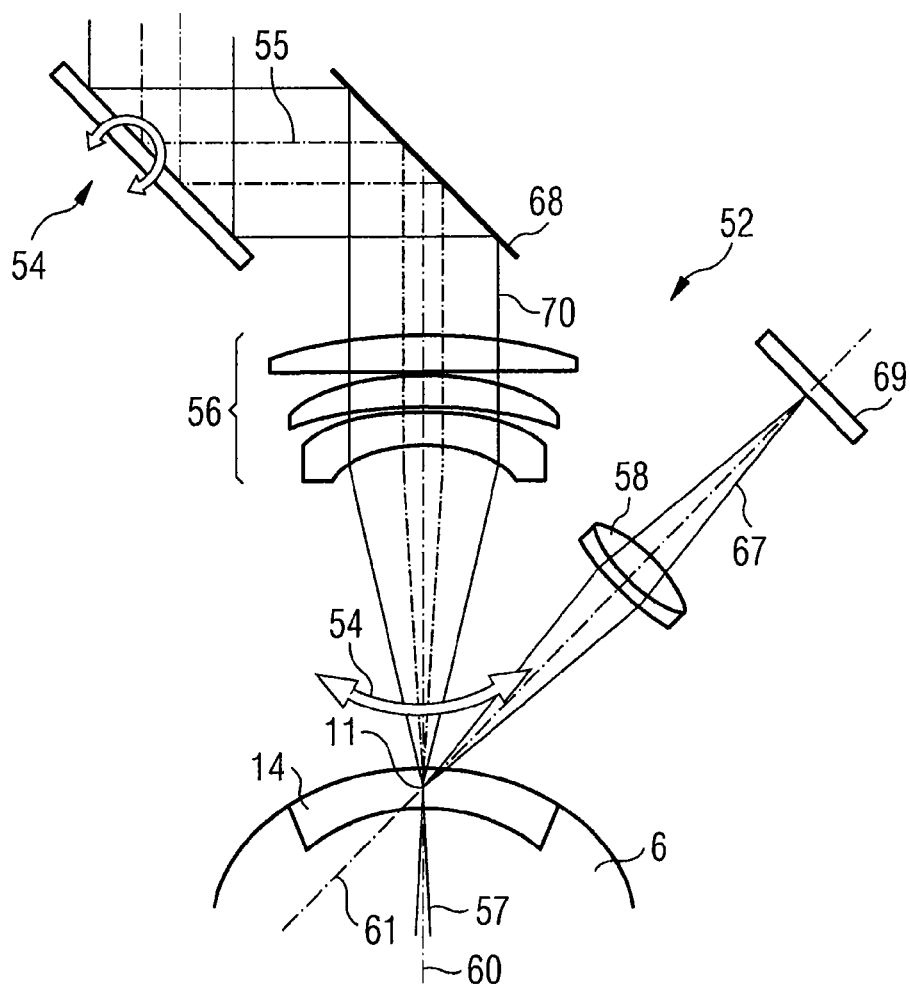
FIG. 16 shows a further embodiment similar to that of FIG. 14.

This principle is shown in FIG. 16, which relates to a variant of the fourth embodiment. The construction of FIG. 16 corresponds largely to that explained with reference to FIG. 14. Identical parts have the same reference numerals and are, therefore, not described again.

The slit-shaped illumination is now incident centrally, i.e. coaxially to the treatment beam 55. This provides an illumination beam path 70, whose optical axis 60 coincides with the optical axis 61 of the treatment beam path. Observation is effected along an optical axis 61 which is located obliquely to the optical axis 60 of the illumination beam path. Thus, the observation beam path 67 is located at an angle to the illumination beam path, as was the case also in the embodiment of FIG. 14. However, in the construction of FIG. 16, the scanning movement of the illumination beam path is caused by a scanning unit 54 that is provided for the treatment beam anyway. The radiation coming from the scanning unit 54 is deviated again, in the construction shown in FIG. 16, through a mirror 68 which may be optionally provided as a beam splitter and enables observation of the field of operation through a microscope.

The scanning unit 54 changes the angle of incidence of the optical axis 60 relative to the eye 6, at which angle the illumination radiation of the illumination beam path 70 is incident on the cornea 14. The observation beam path 67 as well as its optical axis 61 are not adjustable in the embodiment of FIG. 16, although this may be optionally possible, of course, in order to obtain additional information. The scattered-light channel 57 is thus displaced along the (fixed) optical axis 61 of the observation beam path. In the observation beam path 67, an image receiver 69 is arranged following the imaging optics 58, said image receiver 69 recording an image of the scattered-light channel 57 located at the point of intersection of the axes 61 and 60. Evaluation of the image from the image receiver 69 yields information on the size and the position of the plasma bubble 11, and an intensity evaluation of the image in a cut leading through the plasma bubble 11 or a corresponding projection provides a signal similar to FIG. 15.

Figure 17:
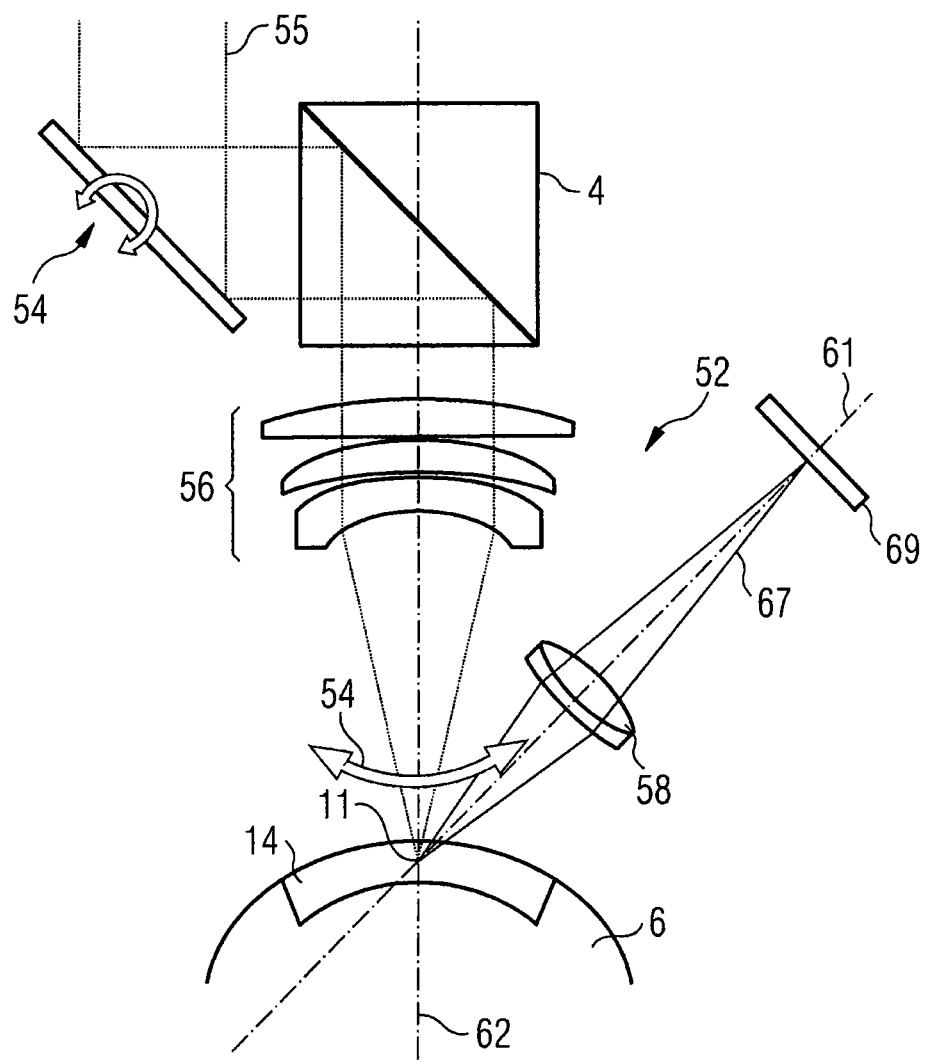
FIG. 17 shows a further embodiment similar to that of FIG. 14.

FIG. 17 shows a further variant of the fourth embodiment of FIG. 16. Parts already shown in FIG. 16 are identified by the same reference numerals and are not explained again. Like the construction of FIG. 16, the slit-lamp arrangement 52 of FIG. 17 also provides an observation beam path 67, whose optical axis 61 extends obliquely to the optical axis 62 of the treatment beam path. In the observation beam path 67, the imaging optics 58 are arranged preceding an image receiver 69. However, no additional illumination radiation is coupled in now, but instead, treatment radiation scattered directly at a plasma bubble 11, or radiation generated in the plasma bubble 11 itself, is detected. Observation is effected from an inclined view, so as to derive depth information from the signal of the image receiver 69. In addition, visual observation by means of a microscope is possible via the beam splitter 4, which no longer serves for coupling in now.

Figure 18:
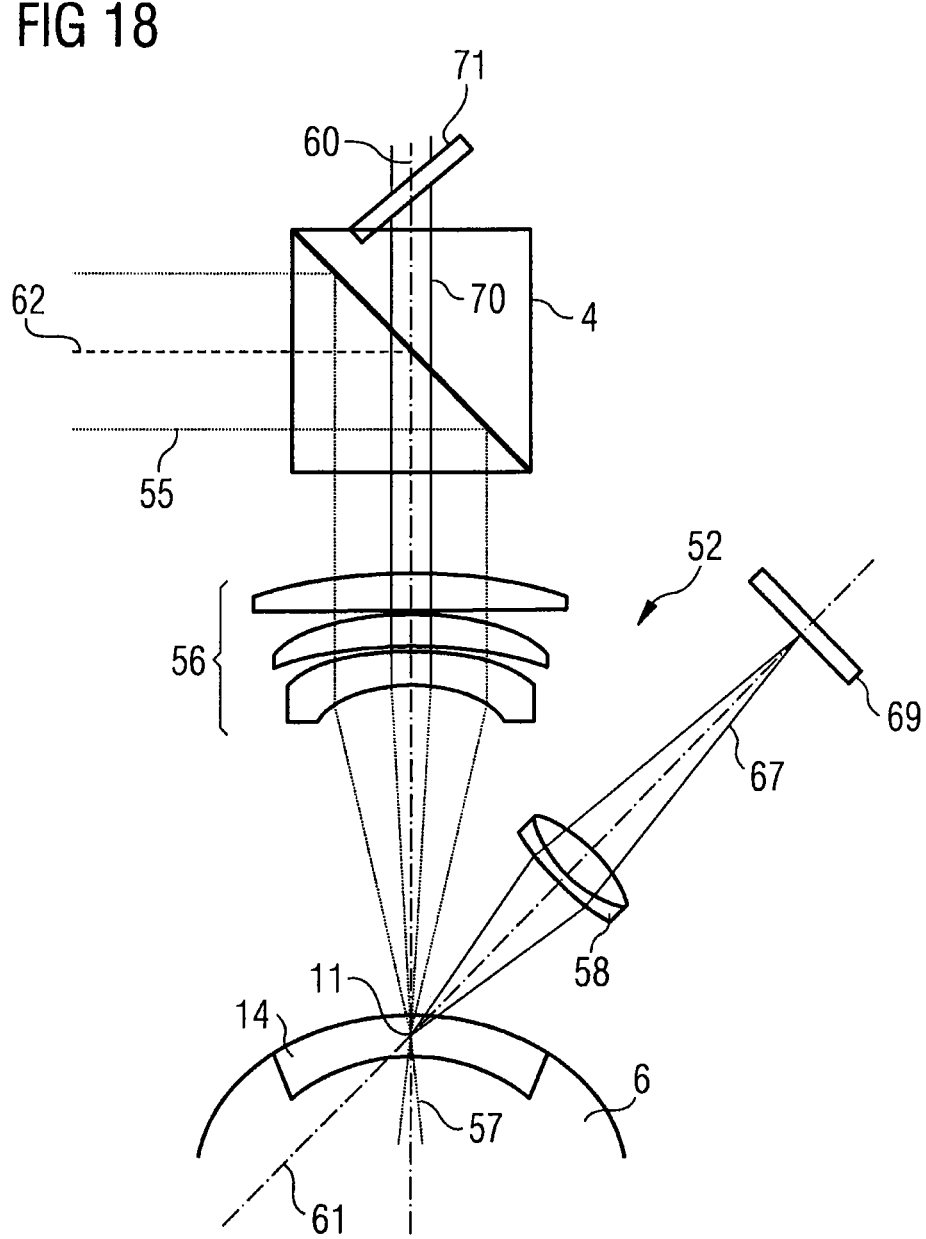
FIG. 18 shows a further embodiment similar to that of FIG. 14.

FIG. 18 shows a further variant of the fourth embodiment. The slit-lamp arrangement 52 which serves as the measurement device in the laser surgical instrument 1, corresponds essentially to the construction of FIG. 17. Now an illumination beam path 70, which irradiates a slit-shaped illumination via the objective 56, along the optical axis 62 of the treatment radiation 55, is coupled in via the coupling-in beam splitter 4. The coupling-in beam splitter 4 combines the optical axis 60 of the illumination radiation with the optical axis 62 of the treatment radiation 55.

An illumination scanning unit 71 is arranged preceding the coupling-in beam splitter 4, said unit carrying out a deflection of the slit-shaped illumination independent of the treatment radiation 55. This allows the scattered-light channel 57, from which scattered light of the slit-shaped illumination reaches the observation beam path 67, to be adjusted also laterally relative to the focus of the treatment radiation. Thus, in addition to the information obtained by the construction of FIG. 16, the signal of the image receiver 69 allows to obtain information on the scattered-light image and, thus, on the structure of the cornea laterally of the focal point of the treatment radiation 55.

Of course, the information obtained through the measurement device of the third or fourth embodiment with regard to position or size of the plasma bubble 11 is used to control the laser surgical instrument, so that open-loop and/or closed-loop on-line control are achieved here as well.

Figure 19:
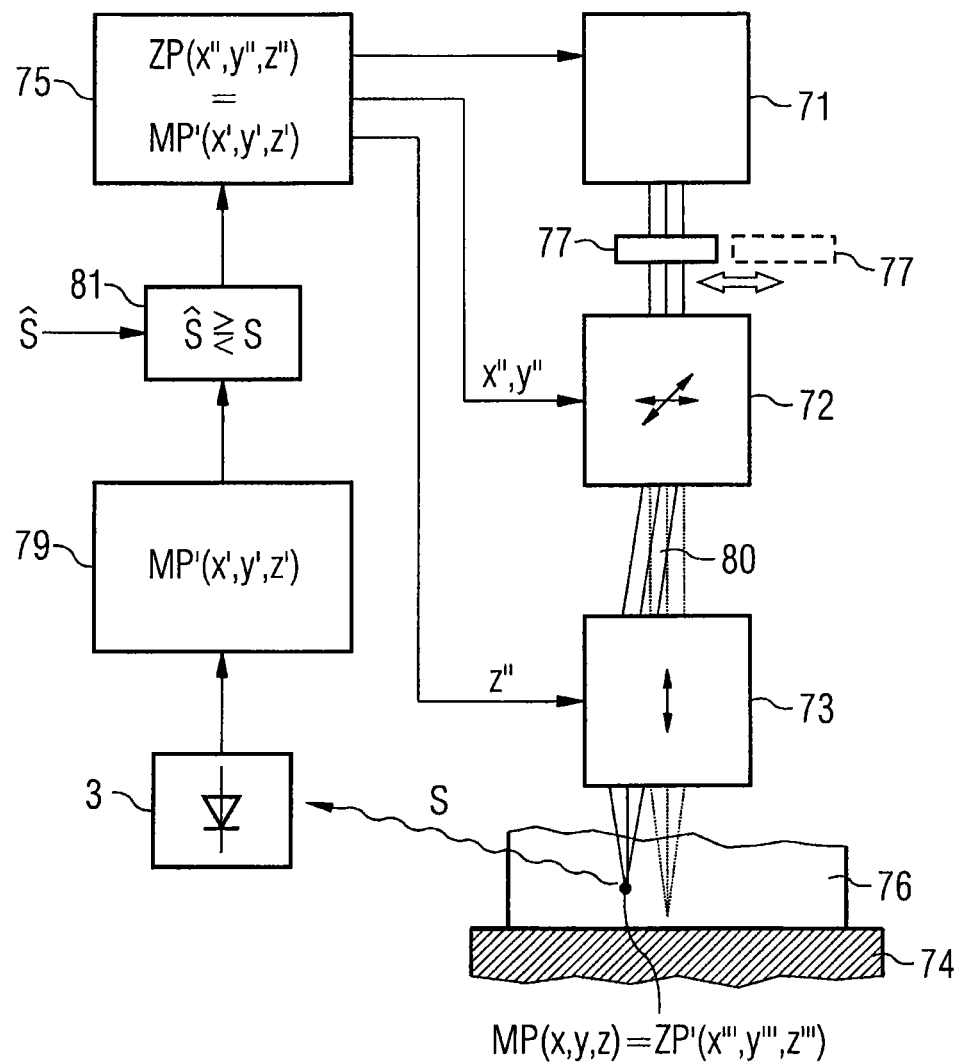
FIG. 19 shows a schematic representation of a further embodiment of the laser surgical instrument of FIG. 1.

FIG. 19 schematically shows a fifth embodiment of a laser surgical instrument, comprising a pulsed source of laser radiation 71 with a pulse energy that is sufficiently large for treatment of the tissue in question; a deflecting unit 72, which laterally deflects the laser beam coming from the source of laser radiation 71; a tunable focusing unit 73, by which the position of the focal point in the depth of the tissue is set; a positioning unit 74 for positioning the tissue 6 to be treated, as well as a control unit 75 for control of the source of laser radiation 71, the deflecting unit 72 and the focusing unit 73. The control unit 75 controls the aforementioned components such that the focus of the laser radiation is sequentially focused on real target points ZP' having the coordinates (x", y", z"). To this end, information on the coordinates (x", y", z") of desired target points ZP has to be available to the control unit 75. Depending on the application, the positioning unit 75 may be omitted, or may be replaced by a device ensuring coarse positioning of the tissue 76.

In the laser surgical instrument of FIG. 19, there are further provided an energy reducer 77, a detector 78 and a memory unit 79. The radiation energy of the pulsed source of laser radiation 71 is attenuated by the energy reducer switched into the beam path to such an extent that the focus of the laser radiation in the tissue 76 will not cause any irreversible changes. The laser beam 80 emitted by the source of laser radiation 71 can thus be scanned in a focused manner in the tissue 76 as a measurement beam (in a so-called regime of measurement), on the one hand, and also as a treatment beam (in a so-called regime of treatment), on the other hand. As measurement beam the laser beam 80 causes a laser-induced signal S in the real measurement point MP as a function of the properties of the tissue said signal S being received by a detector 78 via the detection beam path (which is not shown in further detail). The detected laser radiation-induced signals S are supplied from the output of the detector 78 to the input of a memory unit 79 and are stored in the memory unit 79 together with the coordinates (x', y', z') of the detected associated points of measurement MP'. The laser radiation-induced signals S are compared in a comparator unit 81, which is connected to the output of the memory unit 79, with threshold values S stored therein.

This selects those points of measurement onto which the treating laser beam is to be directed as target points when the energy reducer 7 is inoperative. This defines the regime of treatment. The coordinates of these selected detected points of measurement MP' are transmitted to the control unit 75 and are available to control the deflecting unit 72 and the focusing unit 73.

Transformation of the coordinates of the detected points of measurement MP' into coordinates of the desired target points is not required, because they are based on the same coordinate system. The coordinate system (x', y', z') of the measurement is identical, with regard to the reference point, with that of the target points (x''', y''', z''') as well as with that set for the treating laser radiation. Possible deviations from this identity due to instrument-specific tolerances do not interfere strongly, because they remain constant in all cases and can thus be compensated for.

Figure 20:
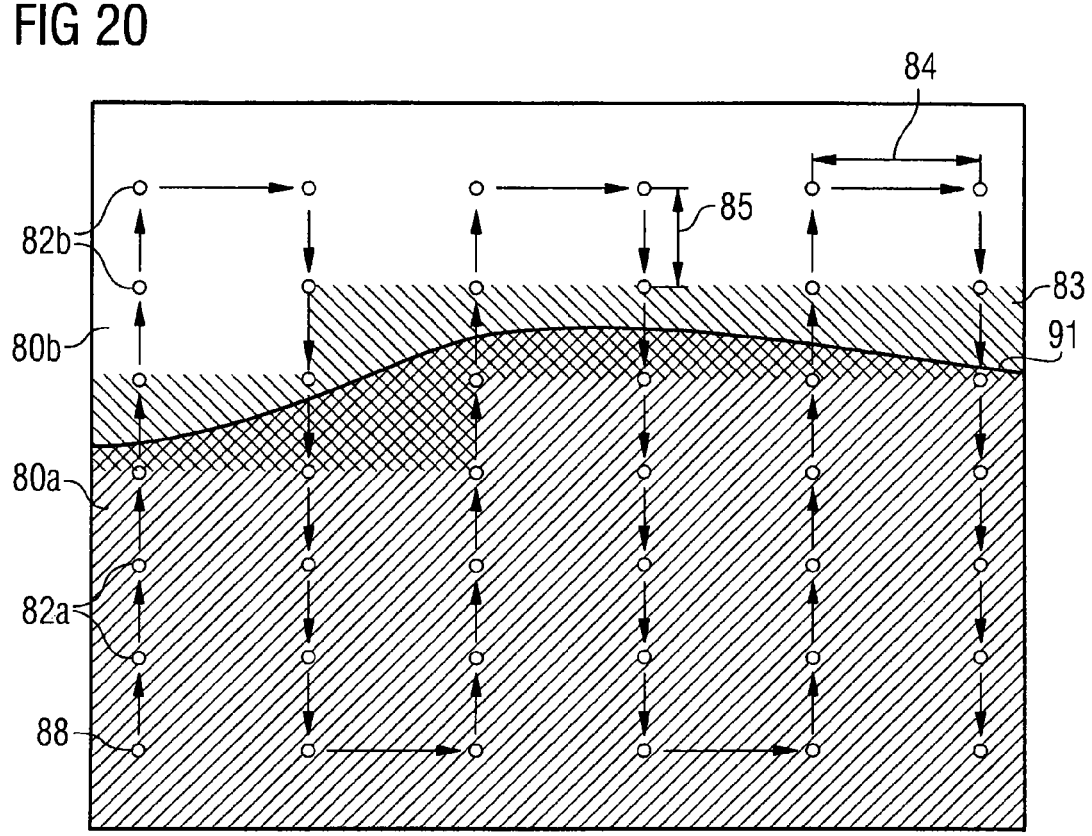
FIG. 20 shows an example of a measurement regime for the scanning of a tissue with the laser surgical instrument of FIG. 19, and FIGS. 21 to 22 show further examples of a measurement regime for the scanning of a tissue with the laser surgical instrument of FIG. 19.

FIG. 20 shows a first regime of measurement for sensing a tissue 76. Beginning at a starting point 88, the laser focus is directed onto points of measurement arranged in a grid. Different types of tissue 80a and 80b, which contact each other at a boundary 91, lead to differently laser-induced signals S. Due to the evaluated signal S, each point of measurement can be assigned to one type of tissue. Thus, the point of measurement 82a is located in the first type of tissue 80a and the point of measurement 82b is located in the second type of tissue 80b. This allows an expected area 83 to be derived for the possible location of the boundary 91. Said area is shaded in FIG. 20 from top left to bottom right. The precision with which the actual location of the boundary 91 can be indicated by the expected area 83 depends on the lateral scanning resolution 84 and on the normal scanning resolution 85.

Figure 21:
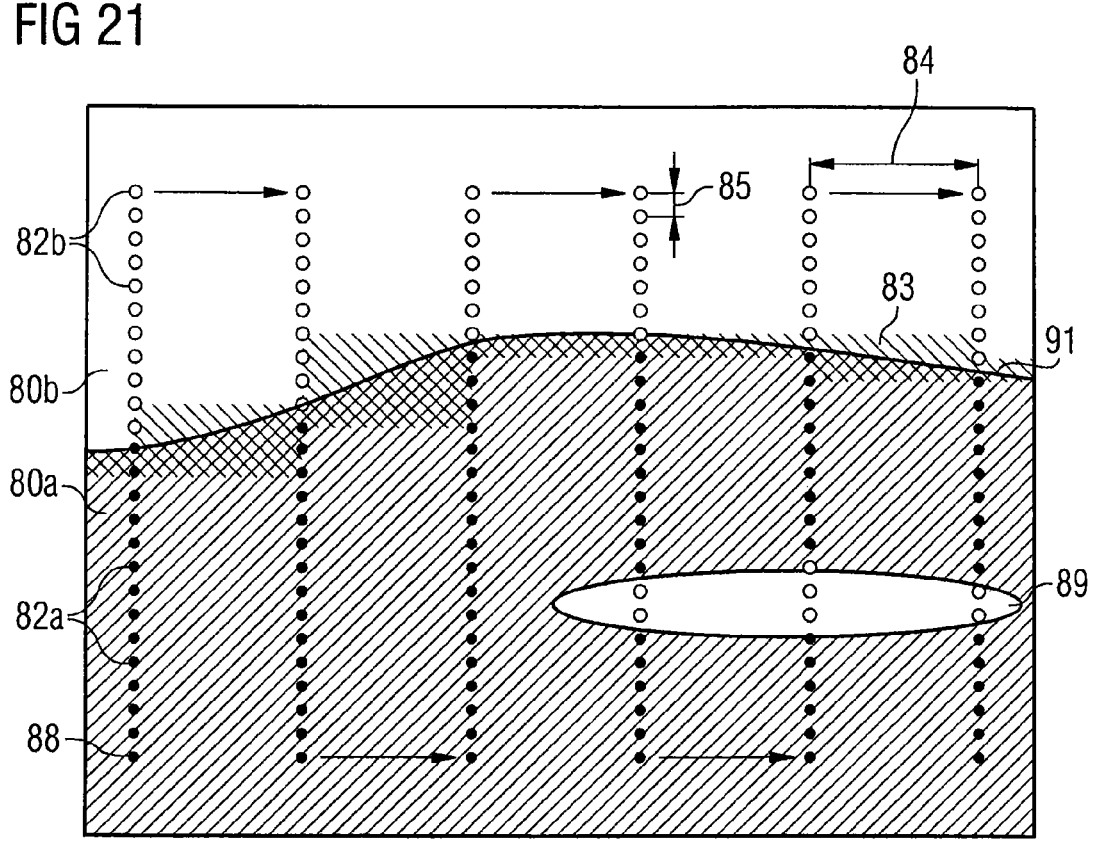

The regime of measurement shown in FIG. 21 differs from that of FIG. 20 by a higher depth resolution, i.e. by a smaller normal scanning resolution 85. The location of the boundary 91 can be determined considerably more precisely for a constant lateral scanning resolution 84, if the boundary 91 extends approximately parallel to the surface and does not have any major slopes. Therefore, depending on the assumed course of the boundary 91, the accuracy of measurement can be increased by providing an asymmetrical scanning resolution, for example by an increase in only one direction, or the number of points of measurement 82 and thus the duration of measurement can be reduced by reducing the scanning resolutions in the other directions. The volume sensing has the advantage that all structures present therein can be recognized. Thus, for example, inclusions 89 are detected equally well as the boundary 91.

Figure 22:
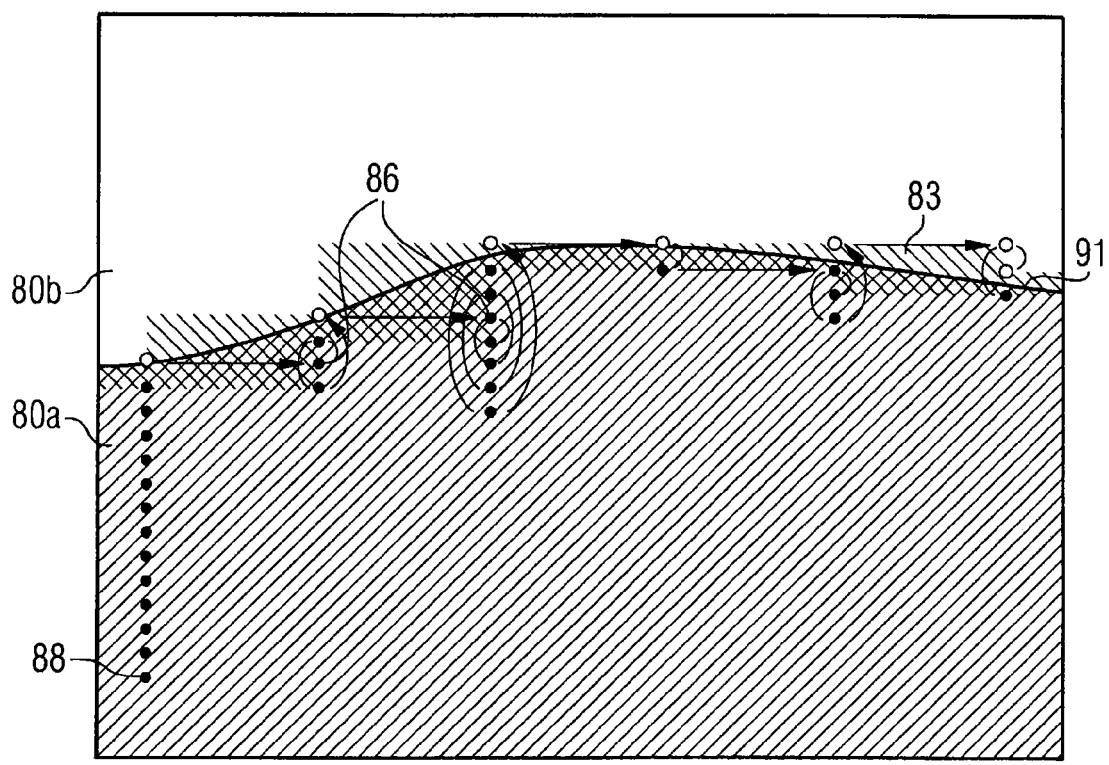

However, if there is only an interest in knowing the location of the boundary 91, the regime of measurement can be changed so as to reduce the duration of measurement, as shown in FIG. 22, which illustrates a third variant of a regime of measurement, which senses the course of a boundary 91 using as few points of measurement as possible, but at high resolution. The sensing starts at a starting point 88, which is known to be located in the first type of tissue 80a. The focus is then displaced, by the predetermined scanning stepping or resolution, toward the assumed position of the boundary 91, and the signal S is evaluated. If the focus traverses the boundary 91, the signal S changes. The depth coordinate of the boundary 91 is thus known for this lateral position. The sensing operation is then continued at the lateral scanning resolution, starting from a new starting point 86 at the same depth. However, instead of moving the focus up or down now, alternating measurements are made at increasing distances from the new starting point 86 above and below the expected depth position of the boundary 91. This is indicated by small bent arrows in FIG. 22.

In this manner, the depth position of the boundary 91 is determined at all lateral points of interest. The better the assumed position of the boundary 91 at the new lateral position matches the actual position, the less points of measurement will be required. Thus, general knowledge about the course of the boundary 91 allows a further reduction of the number of points of measurement required. Such general knowledge exists, for example, for the course of the Bowman's membrane, which is located at an approximately constant depth beneath the outer surface of the cornea and is nearly spherical. Therefore, after several points of measurement, the assumed depth position of this membrane can be predicted rather precisely, and there are only few further points of measurement required in order to determine the exact position.

Also, many tissue structures may be presumed to have a smooth course without depth variations at a large spatial frequency, so that a lower lateral resolution of ca. 0.1 mm may be sufficient. An area having a diameter of 10 mm can then be detected by means of ca. 100,000 sensing points, at a lateral resolution of 0.1 mm and a depth resolution of 1 μm.

The above-described embodiments may be employed in a particularly advantageous manner for the above-mentioned surgical method. To this end, the cornea of the eye can be aspired onto a contact glass and measured at high depth resolution (ca. 1 μm) and low lateral resolution (e.g. 100 μm) from the epithelium to the endothelium, over the entire area in which the surgical operation is to be effected. According to the fifth embodiment, the energy reducer 77 is switched on for this purpose, and the layers of the cornea are sensed at several positions in a lateral 100 μm grid, substantially perpendicular to the surface of the cornea. In the detection beam path, multi-photon fluorescence is then detected, for example, in a spatially resolved manner, at a suitable wavelength which is sensitive to differences in the different layers and/or boundaries. Alternatively, each of the aforementioned principles of measurement may be applied.

A three-dimensional image of the layer of the cornea can be generated from a plurality of thus obtained depth profiles. In said image, the laterally resolved depth position of the Bowman's membrane can be recognized, which may be of importance depending on the cutting path. For the treatment, the energy reducer is removed from the beam path, so that the desired cut is effected below the border of the epithelium when the scanning operation is carried out again. The epithelium thus remains largely uninjured, so that the cut heals again after a few days.

However, it is possible not only to remove the epithelium along the Bowman's membrane, but also to effect a cut located deeper down in the stroma. In doing so, the thickness of the stroma remaining on the epithelium can be precisely set by the previous measurement, thus excluding damage to or loss of the epithelium.

The invention claimed is:

1. A method of measuring and treating a transparent or semi-transparent tissue, the method comprising:
   providing illumination laser radiation;
   focusing the illumination laser radiation at a focal point in the tissue;
   three dimensionally scanning the tissue with the illumination laser radiation by changing the position of the focal point within the tissue in three dimensions;
   detecting tissue-specific signals induced by said focusing;
   assigning the detected tissue specific signals to respective positions of the focal point at which the tissue-specific signals were detected, wherein the respective positions of the focal point constitute points of measurement located within the tissue;
   determining positions of boundaries in the tissue, inclusions in the tissue or both by filtering out the points of measurement at which predefined values were detected for the tissue specific signals;
   defining target points within the tissue based on the points of measurement remaining after the filtering out;
   performing a subsequent treatment of the tissue by focusing treating laser radiation into the tissue and scanning the treating laser radiation over the target points within the tissue;
   wherein the illumination laser radiation and the treating laser radiation are provided from the same laser radiation source; and
   wherein the treating laser radiation and the illumination laser radiation are focused and scanned by the same optical elements.

2. The method as claimed in claim 1, further comprising selecting the target points from the measurement points such that the target points are a subgroup of the measurement points.

3. The method as claimed in claim 1, further comprising repeatedly determining the points of measurement and the target points; and
   applying treating laser radiation to the target points.

4. A device for measuring and treating a transparent or semi-transparent tissue, comprising:
   a source of laser radiation that emits illumination laser radiation;
   a deflecting unit that deflects the illumination laser radiation;
   a focusing unit that focuses the illumination laser radiation at a focal point in the tissue;
   a detector unit that detects tissue-specific signals induced in the tissue by the focused illumination laser radiation; and
   a control unit which controls the source of laser radiation, the deflecting unit and the focusing unit operably interacting such that the position of the focal point is three-dimensionally scanned by the deflecting unit and the focusing unit over a plurality of positions within the tissue;
   wherein the detector unit provides to the control unit signals representing the tissue-specific signals;
   wherein said control unit assigns said signals to respective positions of the focal point at which the tissue specific signals were detected, and wherein the respective positions of the focal point constitute points of measurement within the tissue, and wherein the control unit determines positions of boundaries in the tissue within the tissue, inclusions within the tissue or both by filtering out the points of measurement at which predefined values were detected for the tissue specific signals;
   wherein the control unit further determines target points within the tissue for a subsequent treatment of the tissue by focused treating laser radiation based on the points of measurement filtered out;
   wherein the source of laser radiation also emits the treating laser radiation; and
   wherein the treating laser radiation and the illumination laser radiation are both deflected by the deflecting unit and focused by the focusing unit.

5. The device as claimed in claim 4, wherein the control unit selects the target points from the points of measurement thereby making the target points a subgroup of the points of measurement.

6. The device as claimed in claim 4, further comprising an energy reducer, following the source of laser radiation in the beam path and which is selectably activatable to moderate the laser radiation emitted by the source of laser radiation to provide said illumination laser radiation.

7. The method as claimed in claim 1, further comprising detecting tissue-specific signals by detecting back-scattered illumination radiation.

8. The device as claimed in claim 4, wherein the detector unit detects back-scattered illumination radiation as the tissue specific signals.

* * * * *